US006303115B1

(12) United States Patent
Natsoulis

(10) Patent No.: US 6,303,115 B1
(45) Date of Patent: *Oct. 16, 2001

(54) SCREENING METHODS USING MICROBIAL STRAIN POOLS

(75) Inventor: George Natsoulis, San Francisco, CA (US)

(73) Assignee: Microcide Pharmaceuticals, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/876,691

(22) Filed: Jun. 16, 1997

Related U.S. Application Data
(60) Provisional application No. 60/019,628, filed on Jun. 17, 1996.

(51) Int. Cl.[7] .............................. A01N 63/00; C12Q 1/68; C07H 21/04
(52) U.S. Cl. ........................................................... 424/93.2
(58) Field of Search ............................... 424/93.2, 93.21, 424/93.3; 435/6, 822; 436/800; 536/24.31, 24.32

(56) References Cited

U.S. PATENT DOCUMENTS

| 5,612,180 | * | 3/1997 | Brown et al. | ............................. | 435/6 |
| 5,639,603 | * | 6/1997 | Dower et al. | ............................. | 435/6 |

FOREIGN PATENT DOCUMENTS

| WO 95/02823 | * | 1/1995 | (WO) | ................................. | 435/7.21 |
| WO 96/17951 | * | 6/1996 | (WO) | ...................................... | 435/6 |
| 9623075 | | 8/1996 | (WO) . | | |
| 9723642 | | 7/1997 | (WO) . | | |

OTHER PUBLICATIONS

Kier and Testa. Complexity and emergence in drug research. Advances in Drug Research, vol. 26:1–43, Mar. 1996.*
Zeng et al. Differential cDNA cloning by enzymatic degrading subtraction (EDS). Nucleic Acids Research. vol. 22(21):4381–4385, Nov. 18, 1994.*
Basson et al., "Identifying Mutations in Duplicated Functions in *Saccharomyces cerevisiae:* Recessive Mutations in HMG–CoA Reductase Genes," *Genetics* 117:645–655 (1987).
Boeke et al., "5–Fluoroorotic Acid as a Selective Agent in Yeast Molecular Genetics," *Methods in Enzymology* 154:164–175 (1987).
Hensel et al., "Simultaneous Identification of Bacterial Virulence Genes by Negative Selection," *Science* 269:400–403 (1995).
Ito et al., "Transformation of Intact Yeast Cells Treated with Alkai Cations," *Journal of Bacteriology* 153(1):163–168 (1983).
Lee and Nurse, "Cell Cycle control genes in fission yeast and mammalian cells," *Trends in Genetics* 4(10):287–290 (1988).
Lee and Nurse, "Complementation used to clone a human homologue of the fission yeast cell cycle contol gene cdc2," *Nature* 327:31–35 (1987).
Nelson et al., "Genomic mismatch scanning: a new approach to genetic linkage mapping," *Nature Genetics* 4:11–17 (1993).
Riles and Olson, "Nonsense Mutations in Essential Genes of *Saccharomyces cerevisiae*," *Genetics* 118:601–607 (1988).
Schena et al., "Quantitative Monitoring of Gene Expression Patterns with a Complementary DNA Microarray," *Science* 270:467–470 (1995).
Shalon et al., "A DNA Microarray System for Analyzing Complex DNA Samples Using Two–color Fluorescent Probe Hybridization," *Genome Research* 6:639–645 (1996).
Shoemaker et al., "Quantitative phenotypic analysis of yeast deletion mutants using a highly parallel molecular bar–coding strategy," *Nature Genetics* 14:450–456 (1996).
Sikorski and Hieter, "A System of Shuttle Vectors and Yeast Strains Designed for Efficient Manipulation of DNA in *Saccharomyces cerevisiae*," *Genetics* 122:19–27 (1989).

\* cited by examiner

*Primary Examiner*—Terry McKelvey
*Assistant Examiner*—William Sandals
(74) *Attorney, Agent, or Firm*—Lyon & Lyon LLP

(57) ABSTRACT

Methods of screening for antimicrobial agents or other compounds active on a particular strain are described. These methods use pools of strains of cells or microbes in order to screen for activity on many cellular targets in a single screen. The strain or strains in the pool for which growth is inhibited or stimulated are determined; such identification can also provide a means of identifying the cellular target on which a compound is active.

60 Claims, 7 Drawing Sheets

SCREENING METHODS USING MICROBIAL STRAIN POOLS

RELATED APPLICATION

This application claims the benefit of Natsoulis, U.S. Provisional Application No. 60/019,628, entitled "Screening Methods Using Microbial Strain Pools", filed Jun. 17, 1996, which is incorporated by reference herein in its entirety including drawings.

BACKGROUND

This invention relates to the field of screening for compounds which affect particular microbial strains, particularly including screening for antimicrobial agents.

Traditional screening methods have generally utilized screening one or a small set of compounds at a time against a particular strain, or separately against a relatively small set of strains of some microbe or cell of interest.

SUMMARY

Screening of large numbers of compounds against many strains or potential targets can be an extraordinarily time- and labor-consuming endeavor using conventional screening methods. This invention provides a method for evaluating the effects of one or more compounds or other environmental conditions on individual microbial or cellular strains (cell lines) while avoiding the very high level of work associated with conducting individual assays of the effect on each strain. In particular this provides screening methods which dramatically reduce the work involved in such screening by providing simultaneous screening for compounds active on many different targets in a single solution, where the targets may represent many different cellular functions. In many cases, the number of targets, or variants of targets, screened can extend to hundreds or even more. Thus, the methods are particularly suited to efficient screening of multiple cellular targets against large numbers of test compounds.

The method accomplishes the reduction in the effort associated with screening by using pools of strains rather than screening against individual strains, and distinguishing the individual strains in the pools. The ability to distinguish the individual strains in a pool allows the effect of a test compound on the growth of each of the strains to be determined. The method can be carried out in a variety of different formats, for example using many different types of strains, and any of a variety of techniques for distinguishing the individual strains in a pool.

In the context of this invention, the term "strain" refers to an organism or cell line, and especially to such organisms or cell lines suitable for use in the methods described herein. The term implies that a genetic difference exists between different strains which produces a different phenotype under at least some conditions. The term is not limited to refering to accepted strain designations for particular organisms. Thus, for example, different strains can be different forms of a single species of organism, either naturally occurring or artificially created, different species, or combinations of these. In particular, the term includes, but is not limited to bacterial strains, strains of eukaryotic microorganisms, cell lines derived from complex eukaryotes or higher eukaryotes, including humans, and cells expressing heterologous genes. The prokaryote and yeast cells are examples of a variety of different microbes. The term "microbe" refers to a microscopic organism, but is preferably a unicellular organism or has a unicellular stage in the life cycle.

As indicated above, in a first aspect, the invention provides a method for determining the effect of a test compound on the growth of a strain in a pool of more than one strain. The method involves determining whether the presence of the test compound changes the representation of any of a plurality of strains in the pool of strains. Each of the plurality of strains has a different distinguishable tag. While the method can be used to focus on the effect of a test compound on a single strain, preferably the effects on the growth, and thus the representation in the pool, of a plurality of strains is determined. A change in the representation of one or a subset of the strains in the pool indicates that the test compound acts preferentially on that strain. A change in representation of a strain in response to a test compound can be observed in a number of different ways. For example, in cases where strain growth is consistent, the numbers of a strain in the pool can be directly determined, and will reflect the effects of the test compound. Likewise, the change in representation can be determined by comparing the growth of a strain against the average growth of the pool or against one or more control strains in the pool. Alternatively, the growth of a strain or strains in the presence of a test compound can be compared to the growth of the strain in the absence of the test compound. This will often be combined with comparison of the effects on other strains in the pool. Many other modes for determining strain representations will be apparent to those skilled in the art, including variations and combination of the above.

The number of strains in a pool can vary over a wide range. Preferably, however, the pool has at least 10, more preferably at least 20, still more preferably at least 50, and most preferably at least 100 strains.

The term "growth" means an increase in numbers of cells; negative growth thus refers to a decrease in the number of cells. The term can, for example, refer to an increase in the number of cells in a pool or to an increase in the numbers of cells of a particular strain in a pool. "Changing the growth rate" means altering the rate of change in the number of cells. The change can be an increase or a decrease, therefore such a change in the growth rate can be due to cell killing, cell cycle slowing or arrest, or growth enhancement.

The term "representation" refers to the relative numbers or proportion of a strain or each of a plurality of strains in a mixture or pool of strains. In general, the methods of this invention preferably utilize determination of the representation of the strains in the pools, and the changes in those representations in response to the presence of a test compound. However, absolute or approximate numbers of cells of a strain in the pool can also be used to provide useful information.

A "distinguishable tag" refers to a characteristic of a strain which allows the strain to be conveniently distinguished from others in a pool of strains. Such tags can, for example, be cell surface molecules which differ between strains and which can be readily specifically detected. Other tags which can be used include distinct spectroscopic labels attached to strains, selectable markers such as drug resistance markers and trophic markers, and nucleic acid sequence tags, including tags differing in base sequence and/or length. The tags may be natural to the cells of the strain or may be artificially inserted, such as recombinant tags. Other methods of individually tagging strains to allow the distinguishing of strains in a pool are known to those skilled in the art and can be used in this invention.

From the variety of different types of distinguishable tags, in preferred embodiments the tags are selectable markers or nucleic acid sequence tags, for example, recombinant DNA sequence tags.

A "selectable marker" refers to a specific characteristic of a strain which allows the strain to be selected from other strains not having the marker through the inhibition of growth or killing of such other cells. Common examples of such selectable markers include drug resistance markers, such as antibiotic resistance markers, and trophic markers, such as specific auxotrophic requirements.

A "nucleic acid sequence tag" refers to a nucleic acid sequence which is present in a strain but not in other strains from which it is desired to distinguish the particular strain. Such a sequence tag can be detected as a ribonucleic acid (RNA) sequence or preferably a deoxyribonucleic acid (DNA) sequence. The distinction between strains can be length and/or sequence differences.

In preferred embodiments, the tags are recombinant DNA tags which differ in sequence and which can hybridized with non-cross-hybridizing complementary probes under appropriately stringent hybridization conditions. The tags can be extrachromosomal, such as on a plasmid vector, preferably a single copy vector, or are preferably incorporated in a chromosome of the strain. Also in preferred embodiments, the representation of a strain is determined by hybridizing a complementary probe to the tag, preferably the method uses a mixed probe, which contains representatives of the tags from each strain present in the pool. In embodiments in which nucleic acid (e.g., recombinant DNA) sequence tags are used, it may be beneficial to amplify the tag sequence, thus increasing the numbers of each of the tag sequences and or the sequences complementary to the tag sequences; commonly such amplification is carried out by the polymerase chain reaction (PCR).

In this invention, a "distinguishable recombinant DNA tag" or "distinguishable DNA tag" or "DNA tag" refers to a DNA chain which can conveniently be identified as distinct from other DNA chains in a DNA mixture resulting from growth of a pool of strains of this invention. In different embodiments, the DNA tag may be identified by size, such as fragment size following a particular nuclease digestion(s), such as with one or more restriction endonucleases, or by nucleotide sequence. The tag thus serves as a label to allow a particular strain to be discriminated from the other strains in a pool. For tags which are recombinant, the chain has been moved from its natural molecular environment. Typically, the chain has be inserted from an exogenous source.

In embodiments in which the tags are selectable markers, the representations of the strains are preferably determined by growing the pool on a plurality of selection media corresponding to the selectable markers used. Thus, for example, where drug resistance markers are used, the numbers of a strain having a particular resistance marker can be determined by plating the strain on a growth medium having a concentration of a drug which will prevent growth of any strain which does not have a gene conferring resistance to that drug. Use of such media corresponding to each of the strains for which the representation is to be determined allows the relative effects on growth to be determined.

As previously indicated, a variety of different types of strains may be pooled. Therefore, in preferred embodiments, the pool contains eukaryotic cells, such as yeast cells or human cells. In other preferred embodiments, the pool contains prokaryotic cells, i.e., bacterial cells.

As indicated above, in preferred embodiments the method is used to simultaneously determine the effect of a test compound, or preferably a large number of test compounds, on a plurality of strains in a single test. Preferably, the method involves comparing the representation of each of a plurality of strains following growth in the presence of the test compound(s) to the representations in the absence of the test compound(s). Further preferred embodiments involve selections of tags, cells, labels, and approaches as described above.

Also in preferred embodiments the method uses differential hybridization of probes complementary to the distinguishable nucleic acid sequence tags in the plurality of strains to compare the representations of each of a plurality of strains in a pool. The differential hybridization involves probes from the pool grown in the presence of test compound with probes from the pool grown in the absence of test compound. The effect of a test compound on growth is thus detected as a change in the hybridization of probes for a strain resulting from the presence of a test compound.

In the context of this invention, "differential hybridization" refers to determining differences in hybridization of distinguishable probes to a single target sequence. Preferably the probes have identical sequences but have distinguishable labels. Also preferably in a differential hybridization technique, the hybridization involves joint hybridization of the distinguishable probes to the target sequence, with the difference in hybridization revealed by the signal or signals resulting from that single hybridization.

In preferred embodiments, mixed probes are used to detect the effects of a test compound on strains in a pool. A first mixed probe is obtained from the tags in the pool grown in the presence of test compound and a second mixed probe is obtained from the tags in the pool grown in the absence of test compound. The mixed probes are combined and hybridized to complementary target sequences, such as on a nucleic acid array. The probe molecules are labeled differently for the two mixed probes, so that hybridization of a combination of the two mixed probes will produce a signal in which one of the labels will dominate. Thus, if the representation of one strain is reduced in the test pool mixed probe, the signal from the hybridization corresponding to that strain will be primarily or solely from the mixed probe from the pool grown in the absence of test compound. An example of such a two label system is the use of two color fluroescent labels. The signal produced by the hybridization of the combined mixed probes for a particular strain will be the color which results from the proportionate color combination of the two different probe label colors. The proportionate color combination results from the relative numbers of labeled probes for the particular strain which are present in the respective mixed probes.

The term "mixed probe" refers to a mixture of different nucleic acid probe molecules which will hybridize to different target sequences. In embodiments of the screening methods of this invention, the number of each of the probe molecules in a mixed probe is indicative of the number of cells having the corresponding tag in the pool from which the mixed probe was obtained. Preferably the representation of each of the probes in a mixed probe is approximately the same as the representation of the strain having the corresponding tag. Typically a mixed probe is generated from a nucleic acid preparation from a pool of strains by amplifying (e.g., by PCR) the tag sequences in that nucleic acid preparation, preferably under conditions which minimize bias in the amplification of the different tags present.

A particular useful application of the method utilizes the greater sensitivity of certain mutant strains of a microbe or cell line toward compounds which act on the gene product which is mutated or present in reduced amount. A plurality, preferably a large number of such strains can be pooled, and the strain or subset of strains which are sensitive to a test compound (potential agent) are discriminated from the other strains in the pool on the basis of a change in growth rate. Such discrimination can be performed by tagging each strain with an individually identifiable deoxyribonucleic acid (DNA) tag prior to growth, and determining which tag is present in a lower (more common) or higher representation in the pool after growth in the presence of the test compounds(s). As an example, if the growth of a particular strain in the pool is fully inhibited by the presence of a test compound, the tag from that strain will be missing from the DNA extracted from the pool after a period of growth.

Thus, in a related aspect, this invention provides a method of screening for an agent active on a particular cellular target. The method utilizes a plurality of strains, each of which has a different altered essential gene. Each of those strains also has a distinguishable recombinant DNA tag, and the plurality of strains are mixed to form a pool of strains. Thus, the pool includes a plurality of strains which each have a distinguishable recombinant DNA tag and a different altered essential gene. The strains having altered essential genes are more sensitive to agents which are active on the product of that gene or a related cellular component than are strains having wild type alleles. The pool of strains is grown in an appropriate growth medium in the presence of a potential agent. The method involves determining whether the growth of one or a subset of the strains in the pool is inhibited or enhanced by the presence of the test compound. This involves determining whether the amount or representation of the corresponding DNA tag is decreased or increased. Inhibition or enhancement of the growth of one or a subset of the strains in the pool indicates that the potential agent is active on a particular cellular target or targets, which is likely to be the essential gene altered in the strain or a component of a biochemical pathway in which the activity of a product of the essential gene is necessary.

In the present context, "method of screening" refers to a method for determining whether a compound has a desired biological activity, and indicates that the method is suitable for characterizing activities of large numbers of compounds (e.g., hundreds or thousands or more), rather than being limited to the evaluation or testing of a relatively small number of compounds.

Stating that an agent (a compound) is active on a particular cellular target, such as the product of a particular gene, means that the target is an important part of a cellular pathway which includes that target and that the agent acts on that pathway. Thus, in some cases the agent may act on a component upstream or downstream of the stated target, including on a regulator of that pathway or a component of that pathway.

In this invention, an "essential gene" is considered to be one which is beneficial for competitive cellular growth in vitro in a medium appropriate for growth of a strain having a wild-type allele corresponding to the particular gene in question. Therefore, if an essential gene is inactivated, that cell will grow significantly more slowly, or not at all in the medium. For screening for antimicrobial agents, it is preferable, though not necessary, that the essential gene is necessary for cellular growth in the medium.

Reference to "different altered essential genes" indicates that each of the essential genes in question is produced in a different form or manner than each of the other of those genes. The changes can be different changes to a single gene and/or changes to different genes. Each of the genes is changed, such as by a change in the nucleotide sequence of the gene which results in a change in the amino acid sequence of the gene product (e.g., by addition, deletion, or substitution of one or more amino acids). Likewise the alteration may be a change which results in a change in the amount of active gene product produced under a relevant growth condition. Such alterations can include alterations to the promoter sequence. Some alterations may be conditional or suppressible in some conditions.

The term, "wild-type allele" indicates that that form of the gene is the one normally present in natural populations of the organism. Mutant alleles thus have at least one nucleotide sequence difference from the wild-type allele.

Indication that an altered gene is "more sensitive" or "hypersensitive" as compared to a wild-type allele of that gene, means that the growth of a strain having the altered gene is affected to a greater extent under at least some relevant growth conditions than a strain which is isogenic except for having a corresponding wild type allele.

In reference to the strains in a pool of strains, "subset" refers to some, but not all of the strains in the pool. In the screening methods of this invention, inhibition of essentially all the strains in a pool by a particular compound suggests that the compound is generally toxic, and that its activity is unrelated to activity specifically or preferentially on any of the altered genes. Thus, usually it is preferable that a potential agent have activity on only one or only a few of the strains having functionally independent gene alterations.

Stating that the growth of a strain is "inhibited" or "enhanced" means that fewer or more, respectively, of the cells of the strain are produced under particular relevant growth conditions.

As indicated above, tags having different lengths may be utilized; a use of such tags is described in Benton et al., SIZE-BASED MARKER IDENTIFICATION TECHNOLOGY, U.S. application Ser. No. 08/770,246, filed Dec. 20, 1996 now U.S. Pat. No. 5,962,249; International Appl. PCT/US96/20406, International Publ. No. WO 96/40979, hereby incorporated by reference. In other embodiments, DNA tags are used which may be of the same length but which have distinguishable sequences. Thus, in a preferred embodiment the distinguishable DNA tags are specific sequence tags.

"Specific sequence tags" refers to DNA or other nucleic acid tags as described above which are individually distinguishable within a group of such tags or in a mixture of nucleic acid sequences (e.g., DNA sequences) and relates to identifying individual tags in this invention based on having distinct nucleotide sequences. In this invention, such specific sequence tags are generally identified by their ability to hybridize to complementary sequences under appropriately stringent hybridization conditions.

For nucleotide (e.g., DNA) chains, such as the DNA tags, "complementary" means that two nucleotide chains or portions of chains have nucleotide sequences which can Watson-Crick base pair with each other over substantially the entire length of the shorter chain or of the complementary portion of a chain.

In many cases it is helpful to provide a strain or strains having wild type alleles corresponding to the altered essential genes. Comparison of the effects of a potential agent on the strain having an altered essential gene or on the strain having the wild type allele serves as a control and an indicator of the specificity of the agent acting on that particular gene product. Thus, in a preferred embodiment, a strain or a plurality of strains is included in the pool which have wild type alleles corresponding to the altered essential gene alleles. In the case where all of the strains having altered essential genes represent alterations of genes endogenous to a particular strain, then only a single wild type strain will be required. However, if the altered genes are homologous genes from a different organism or a different strain, then preferably a separate strain is included having an exogenous gene corresponding to each of the altered exogenous genes. In either case, each of the strains having wild type alleles is labeled in the same manner with a distinguishable DNA tag.

In usual practice, the use of a control pool of strains which is not exposed to the test compound is beneficial to provide more reliable test results. Also, the detectability and reliability of the results is much improved by amplification of the specific DNA tags, typically by PCR amplification. Therefore, in a preferred embodiment, the pool of strains is grown in the presence and absence of the potential agent. After a period of growth, the distinguishable DNA tags are amplified (e.g., PCR amplified) and the presence or absence or relative amount of a particular DNA tag in the amplification product pool is determined by hybridizing those amplification products to a nucleic acid (e.g., DNA) array. Such an array includes a set of nucleic acid molecules which have sequences which are the same as the recombinant DNA tags or sequences complementary to those tags or portions of such sequences which provide sufficient specificity and which do not cross-hybridize. The array elements are thus made up of those nucleic acid sequences. Generally the elements of the array are distributed discretely over the surface of a generally flat device, such as a glass slide. Usually an orthogonal grid or similar regular pattern is used. The effect of the test compound on the growth of a strain is thus indicated by the amount of amplified tag from the pool grown in the presence of the test compound as compared to that from the pool grown in the absence of the test compound.

In the context of nucleic acid, e.g., DNA, chains in this invention, "amplified" means that the number of chains having a particular sequence or a complementary sequence is increased by artificial manipulation.

Also in the context of DNA tags and the oligonucleotide arrays, stating that a nucleotide sequence is the "same as" another, means that the chains have the same nucleotides at the corresponding positions of the chains with no more than minor differences over the length of the shorter chain. Thus, for example, in some circumstances, a DNA tag and the corresponding array oligonucleotide may differ in nucleotide sequence at an end, or by the absence of one or a few nucleotides from one sequence, or by a single base substitution.

A variety of methods may be utilized to distinguish the strains in the pool of strains. In addition to the embodiment above utilizing hybridization to complementary DNA arrays, it is also possible to distinguish particular DNA tags by manipulating the sensitivity to endonuclease digestion so that nucleic acid chains derived from strains for which the growth is affected by a test compound will have different digestion characteristics than strains which were not affected by the test compound. Thus, in another preferred embodiment, the pool of strains is grown in the presence and absence of a potential agent and the inhibition of growth of a strain is determined by amplifying the DNA tags from both the pool grown in the presence of a potential agent and the pool grown in the absence of potential agent. In one approach, the amplified DNA tags from the pool of strains grown in the absence of the potential agent is digested with a restriction endonuclease which cuts the DNA tag sequence in the primer region leaving a 3' overhang. The amplified DNA tags from the pools of strains grown in the presence and absence of the potential agent are then mixed, denatured, and reannealed. The mixture of tags is then digested with a nuclease which does not appreciably digest double-stranded DNA (dsDNA) having 3' overhangs, which will digest dsDNA having a blunt end or 5' overhang. A particular appropriate example is the exonuclease, exoIII. The presence of a particular DNA tag after the exoIII digestion indicates that the potential agent is active on the particular altered gene in the strain carrying that tag. The method can similarly be practiced using an endonuclease which leaves a 5' overhang and an exonuclease which will cleave dsDNA having a blunt end or 3' overhang, but will not appreciably digest dsDNA having a 5' overhang. Those skilled in the art will recognize appropriate nucleases for these uses.

In reference to the action of a nuclease (e.g., a restriction endonuclease or an exonuclease), "digestion" or "digested" indicates that a nucleotide chain(s) has been subjected to the enzymatic cleavage action of the nuclease. If the enzyme can act on the sequence, the result is one or more cuts (which may produce smaller fragments) or partial or complete degradation of the chain.

These methods are suitable for use with a variety of types of microbes or cells. In preferred embodiments, the pool of strains includes a plurality of bacterial strains, or a plurality of fungal strains. In a further preferred embodiment in which the pool includes a plurality of fungal strains, at least one of those strains has an altered essential gene from a different strain or species. Typically, but not necessarily, the strain will be of a genetically manipulable species such as Saccharomyces cerevisiae, and will carry a null mutation in an endogenous essential gene which is complemented with a homologous gene from another strain or species (usually from a pathogenic species). The exogenous gene is generally carried on a plasmid.

Amplification of a sequence may be carried out by a number of different methods, however, the polymerase chain reaction is most commonly used. Thus, in cases in which the distinguishable DNA tags are amplified, in preferred embodiments PCR amplification is used.

In another aspect, this invention provides a method of making an antimicrobial agent by screening for the agent by determining the ability of the agent to specifically inhibit the growth of a microbial strain in a pool of microbial strains. The pool includes a plurality of strains having different altered essential genes and the agent is active on the particular essential gene altered in the growth inhibited strain or on a gene homologous to that particular essential gene. The method also includes synthesizing the antimicrobial agent in an amount sufficient to provide the agent in a therapeutically effective amount to a patient. In a preferred embodiment, the agent is combined with a pharmaceutically acceptable carrier.

In the context of this method, "homologous" indicates that the nucleotide sequences of two genes and/or the sequences of the gene products (e.g., amino acid sequences) have significant similarity, and that the gene products perform a similar cellular function. Thus, two homologous genes may have sequences which have 50, 60, 70, 80, 90, or greater percent nucleotide sequence identity.

The term "synthesizing" refers to a process of chemical reaction step(s) to prepare a molecule from one or more reactant molecules. Thus, the term includes both biosynthesis by an organism (such as a microbe or a plant) and chemical synthesis (i.e., in vitro synthesis, which may utilize enzymes or other cellular synthetic components). It is understood that the synthesis will generally include purifying the desired compound from other undesired molecules.

A "therapeutically effective amount" of an antimicrobial agent is an amount of the agent which relieves, to some extent, one or more of the symptoms of the infection, and includes curing an infection by a microbe susceptible to the agent. Curing means that the symptoms of active infection are eliminated, including the elimination of excessive numbers of viable bacteria of those involved in the infection. However, certain long-term or permanent effects of the infection may exist even after a cure is obtained (such as extensive tissue damage).

In another aspect, strains having distinguishable tags can be used in a growth environment, particularly in an in vivo environment, and the fate of one or more individual strains in a pool of strains monitored. In this method, a pool of tagged strains is placed in the particular growth environment, and the presence of one or more of the strains in sample(s) recovered from the environment is determined. Change in the presence of a strain is indicative of the response of the strain to the environment. Preferably the growth environment is an in vivo environment in a multicellular organism, preferably a vertebrate organism and more preferably a mammal, and the strains are microbial strains. In particular this provides a method for evaluating the efficacy of an inhibitor against one or more of the strains in that in vivo environment, e.g, in an infection model. In preferred embodiments, the strains, tags, and methods for determining the representation of the strains are as described above for the screening methods.

The term "in vivo environment" means on or preferably within a multicellular organism, preferably a vertebrate organism, and more preferably a mammal.

In the context of this method, the term "presence" refers to the numbers of cells in a strain which can be recovered from the test environment. Thus, a reduction in the presence of a strain refers to a reduction in the numbers of the cells of the strain which can be recovered. Usually this will be determined by comparing the numbers of cells recovered from a test organism (following administration of an inhibitor) with the numbers recovered in the same manner from a control organism (no inhibitor administered). It can also or instead be determined by comparing the numbers of cells of a strain recovered from a test organism at two or more time points following the administration of the inhibitor. As in the screening methods above, the presence of a strain is determined by determining the presence of the corresponding tag in a sample.

Other features and advantages of the invention will be apparent from the following description of the preferred embodiments and from the claims.

BRIEF DESCRIPTION OF THE FIGURES

In FIG. 5B, the compound reduces the growth rate of the sensitive strain, but does not reduce the number of viable cells, and so is probably not cidal. 5B also shows that a slow growing strain can be used in a pool with faster growing strains, as the sensitive strain under grows the other strains in the pool by about 200-fold, while the reduction in growth of this strain in the presence of the drug can still be detected. The reduction in growth is about 10-fold.

DESCRIPTION OF THE PREFERRED EMBODIMENTS

I. Overview

The methods of this invention provide an accelerated process of screening a collection of compounds against a collection of strains in order to determine the sensitivity or resistance of each strain to each compound. If assays were performed in which one compound was tested against one strain, the total number of assays which would need to be performed to analyze the compounds against the strains would be equal to the number of compounds times the number of strains. This can be regarded as a two-dimensional array.

The number of assays needed to analyze all combinations in the array can be reduced by effectively compressing the array in either of the two dimensions. Thus, one could screen against individual strains using pooled compounds. However, the number of compounds which can be effectively pooled is limited to about 14, and each compound must be present in at least two pools to allow the effect of each compound to be distinguished. In addition, the pooling of the compounds often limits the concentrations of each test compound, limiting detection to only the most active compounds.

In contrast, the present invention compresses the array by pooling the strains. Generally, the pooled strains are exposed to one test compounds at a time. In order to determine the effect of the test compound on each strain, the strains are individually marked in a manner which allows the individual detection of each strain in the pool. This can be accomplished in various ways, including the following.

For pools containing a small number of strains, e.g., about 10 or fewer, the strains can be marked genetically, such as by incorporating different prototrophy/auxotrophy combinations or drug resistance markers. In this case, the representation of each strain in the pool following growth under test conditions (e.g., the presence of test compound) is determined by plating the pool on appropriate selective media. This is illustrated for a single strain by Example 1 below.

Figure 1:
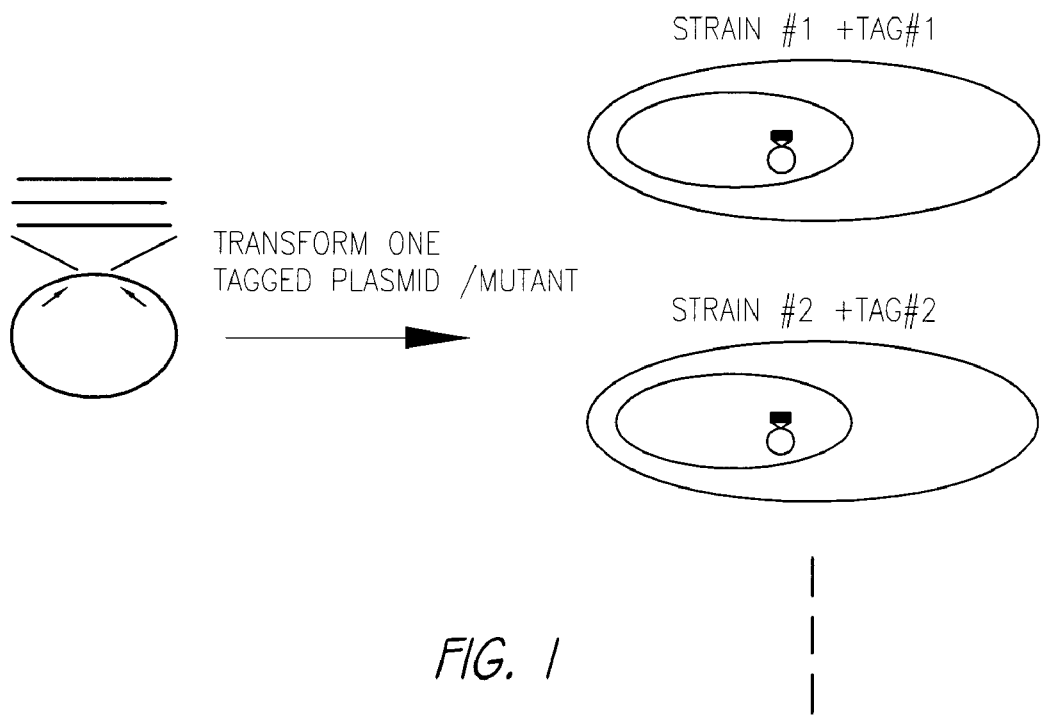
FIG. 1 is a schematic illustrating the creation of tagged mutant strains, each having a distinct DNA tag.

For pools which may contain larger numbers of strains, each strain can be tagged with a specific, individually detectable nucleic acid, e.g., DNA sequence. An example is shown schematically in FIG. 1, in which individual mutant strains are transformed with plasmids containing distinguishable tag sequences. Such a DNA sequence can be any sequence which is specific to a strain thereby allowing specific detection of the presence of that strain in a particular pool of strains. Therefore, the sequence need not be absolutely unique, but only different from sequences in other strains in the pool in a manner allowing the strain to be distinguished. Most commonly the tag will be a recombinant sequence differing in length or sequence or both from recombinant tags in other strains. Preferably a recombinant specific sequence tag is used. With this approach the tag sequence can be recovered from the cells after growth in the presence or the absence of test condition, e.g., the presence or absence of a test compound. The tags can be recovered, amplified, and labeled in a single reaction using PCR. The amplified and labeled PCR products can then be used as a mixed probe in a hybridization assay using an array of the tag sequences immobilized on a solid support. The intensity of the hybridization signal is indicative of the representation of each tag in the pool. Each strain in the pool will generally have a slightly different growth rate, and these differences will be amplified during the growth period. The effect of the test compound on a particular strain can be determined by subtracting out the representation of that strain in a control pool grown in the absence of test compound from the representation of the strain in a pool grown in the presence of the test compound.

Figure 2:
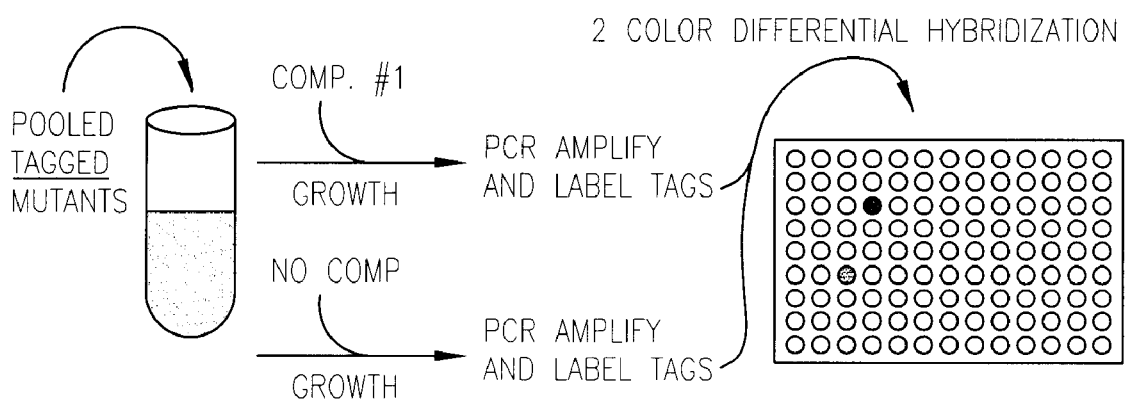
FIG. 2 is a schematic illustrating the detection of the effects of a compound (comp.#1) on a strain in a pool of strains, using 2-color differential hybridization on an oligonucleotide array.

The differential hybridization, i.e., the effect of the test compound, can be determined in various ways, including a fluorescent color test. In this method a combination of two mixed probes is used in the hybridization; the two mixed probes are labeled with fluorescent labels which produce different colors. One mixed probe is derived from the pool grown in the presence of test compound and one mixed probe is derived from the control pool grown in the absence of test compound. For example, the test pool probe can be labeled with fluoresceine (green) and the control pool probe can be labeled with lissamine (red). Thus, if the growth of a strain is inhibited in the presence of a test compound relative to the growth of other strains in the pool, so that its proportional representation is less in the test pool than in the control pool, a greater proportion of the bound probe will have the lissamine (red) label and the corresponding hybridization signal will be red. On the other hand, if the test compound stimulates the growth of a particular strain relative to other strains in the pool or if the particular strain is more resistant to the compound than other compounds in the pool, a greater proportion of the bound probe will have the fluoresceine (green) label and the hybridization signal will be green. Likewise, if the compound does not affect a particular strain or affects all strains in the pool to a similar degree, the relative representation of the strain in the test pool and the control pool will be similar. Therefore, the amounts of the two differently labeled probes which bind to the corresponding tag will be similar and the hybridization signal will be yellow (combined green and red). This approach is shown schematically in FIG. 2.

However, in some embodiments, a change in the growth rate of a strain can be determinded without differential hybridization, using a hybridization of the probes from the test pool but not requiring a hybridization of the probes from a pool grown in the absence of test compound. (Hybridization of probes from the pool grown in the absence of test compound may still be used as an additional growth control.) In such embodiments, the disappearance or reduction (or increase) of the representation of a strain is directly an indication that the test compound is active against that strain. Among other possibilities, this is likely to be practical for pools in which the strains have similar growth rates in the absence of test compounds or for strains which normally maintain approximately the same representation during pool growth in the absence of test compound. For embodiments in which such a semi-quantitative hybridization approach is used and in which the strains have different altered essential genes, it is advantageous to also use one or more control strains having wild-type genes corresponding to the altered genes as growth controls. Use of such controls also provides additional indication of target specificity.

Other methods of tag recovery and detection can also be used, in accord with techniques known to those skilled in the art.

In addition, the pooled strains can also be utilized in a combination method using pooled test compounds. Because each strain is detected individually, the effects of the pooled compounds on each strain can be analyzed in a manner similar to the analysis performed when single strains are used.

Preferred embodiments of the methods of this invention utilize an approach which can be termed "genetic potentiation". Genetic potentiation refers to the greater sensitivity of a microbial strain or cell line having a particular genetic alteration toward compounds which are active on the product of the corresponding gene, as compared to a wild-type strain. As an example, such greater sensitivity, or hypersensitivity, was demonstrated in the case of thermosensitive DNA gyrase mutants of *Salmonella. typhimurium*. (Described in Boggs et al., SCREENING FOR MODULATORS OF BIOMOLECULES, U.S. application Ser. No. 08/589,257, filed Jan. 23, 1996; International Appl. No. PCCT/US96/00916, International Publ. WO 96/23075, hereby incorporated by reference.) Different mutant alleles show hypersensitivity to gyrase inhibitors (e.g., norfloxacin, coumermycin, and ciprofloxacin) relative to a wild type (WT) strain. These mutants however are no more sensitive than WT to antibiotics targeted against other functions. A drug screen for compounds specifically affecting *S. typhimurium* gyrase mutants would thus be both more sensitive and more specific. This strain, however, is only potentiated for one of the many essential functions. In order to detect, in such a sensitive way, growth inhibitors targeted against other functions, one should screen many conditional mutants in parallel, each affected in a different essential gene.

Strains suitable for genetic potentiation methods can be identified from strains having a number of different types of genetic alterations. Notable examples include temperature sensitive mutants (or other conditional growth mutants), and strains which produce a marginally sufficient quantity of a particular gene product (hypomorphs). Generally, the altered gene products of conditional growth mutants will be partially crippled at semi-permissive conditions, and will therefore show enhanced susceptibility to agents acting on that gene product. However, many conditional growth mutants will show such enhanced susceptibility even under permissive conditions.

In using pools of strains to screen for compounds active against a particular strain or cellular target, a variety of different strain discrimination methods can be utilized.

One approach to discriminating between the strains in the pool is to convert the negative report of no growth into a positive report. This approach can be highly sensitive, and will allow pooling of nearly unlimited numbers of mutants. One way to do this is to manipulate the sequence tags after growth in a manner which creates hybrid sequence tags which are resistant to digestion by a particular nuclease, and which are present only if the growth of a strain is inhibited in the pool in the presence of test compound. An example is described below using KpnI and exoIII, however, other selections of one or both enzymes will be apparent to those skilled in the art.

Instead of using a positive report, the absence of a tag can be detected directly by hybridizing PCR amplified postselection tags to a DNA array which includes oligonucleotides having the same sequence as the tags in pre-defined positions in the array. If labeled PCR amplification products are used, the complete inhibition of a strain is indicated by the absence of the tag corresponding to that strain from the post selection pool, which is shown by the lack of signal at the corresponding position in the array. Labeled wild type strains can provide a growth control.

Thus, the main features of an embodiment of the method using a complementary DNA array, as described herein, are as follows:

assay: differential growth of pairs of strains one carrying a mutant (sensitized) and one carrying a wild-type copy of a target gene each strain is tagged with a specific DNA sequence pairs of strains are pooled and grown together pools are grown in the absence of selection (control) and in the presence of selection (addition of a chemical compound). For growth conditional mutants, growth will usually be performed under semi-permissive conditions, so that the altered gene product is partially crippled.

total DNA, including the tags, is prepared at the end of the growth period tags are recovered and amplified by PCR (all tags are flanked by the same sequences, so that one pair of primers can amplify them all)

the PCR product is labeled, preferably with a fluorescent marker.

an array composed of all the sequence tags immobilized on a solid support is prepared the test PCR probe (+chemical) and the control are labeled in two different colors (e.g., two different fluorescent labels) and are used as hybridization probes against the array.

after normalization, the difference between the two signals is indicative of differential growth in the two conditions.

Figures 3, 4:
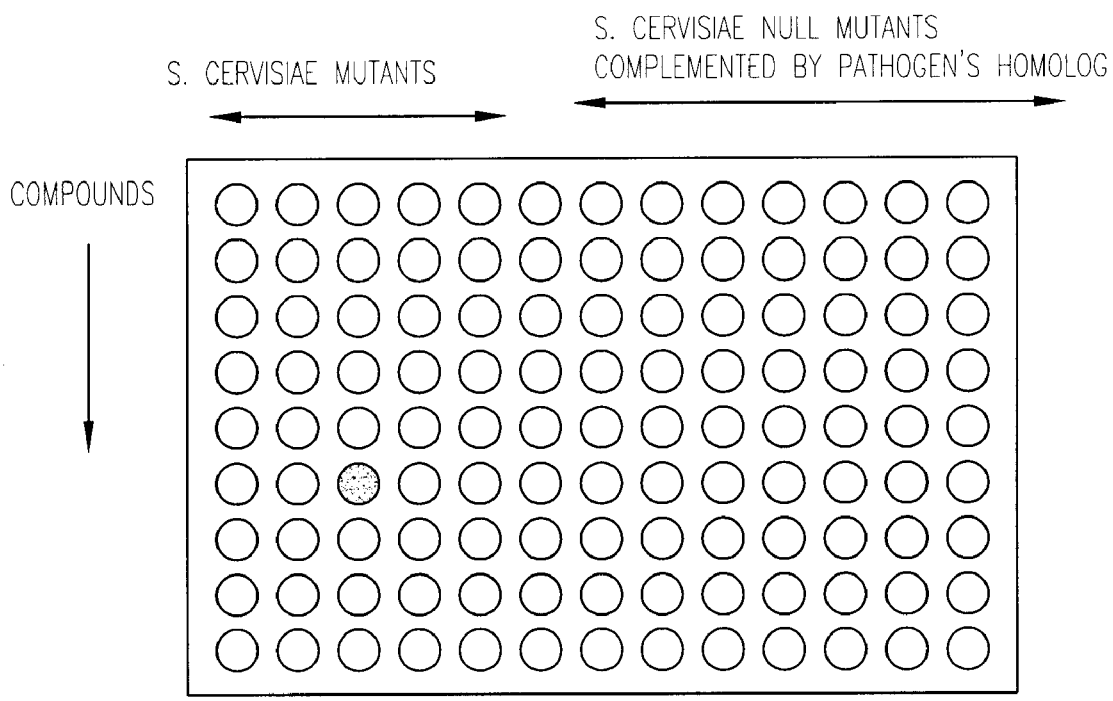
FIG. 3 is a schematic representation of a hybridization array for simultaneous determination of the effects of a number of different compounds on a number of different *S. cerevisiae* mutants. Those mutants include both mutants of *S. cerevisiae* having mutations in endogenous genes, and *S. cerevisiae* strains having mutations in homologous genes from pathogenic species. Strains of this second type have null mutations in the corresponding homologous *S. cerevisiae* genes.
FIG. 4 schematically illustrates the method of discriminating pooled strains by differential sensitivity to exonuclease digestion, in this case exoIII digestion, of DNA tag sequences. The only tags resistant to digestion are from a strain(s) having a wild-type allele corresponding to the mutant allele of a strain whose growth is inhibited by a test compound. The short arrows on the 3'-ends of the hybrids indicate exoIII digestion.

A schematic example of an array is shown in FIG. 3. The array contains tag sequences corresponding to a set of *S. cerevisiae* mutant strains and a set of *S. cerevisiae* null mutants complemented with genes from a pathogenic species. Each of the rows represents a strain pool grown in the presence of a different test compound.

The general methods indicated above can be applied in many screening contexts. A large portion of traditional drug screens can be adapted to this format. Examples of appropriate use contexts include, but are not limited to the following:

If the pair of strains is a mutant versus wildtype in any essential gene of any microorganism, the method can be used to discover antibacterial or antifungal agents The mutant gene need not be from the same species as the recipient strain. This would allow using a genetically manipulable species containing a null mutation in an essential gene, complemented by the homologous gene from a (hard to work with) pathogenic organism. The pathogen's gene is mutated in order to potentiate it relative to its wildtype counterpart. One requirement is that the gene from the pathogen complements functionally, but that's not problematic because the recipient organism can be selected to satisfy this requirement. The recipient is preferably closely related to maximize chances of complementation and easily manipulable genetically.

Sequence relatedness is a relative concept. Some human genes can complement homologous yeast genes. In those cases, the same setup can be used. A potentiated (and a wildtype control) version of the human gene is used to complement a null mutation in a homologous gene of a model organism. The resulting pair of strains is introduced in the same screen.

One does not need to know the function of the human gene or of the model organism gene (e.g., yeast gene).

It is enough that the phenotype of the yeast mutation can be turned into a growth/no growth phenotype and that the human gene complements this. One can thus screen for inhibitors of genes of unknown function whose alteration in human cells causes undiscovered disease. Later if it is found that that gene is implicated in a particular disease, one already has an inhibitor.

The methods allow screening for inhibitors of a broad variety of functions, literally in the same tube.

II. Initial Selections for Screen

A. Selection of Organism for Screen:

The methods of this invention are appropriate for use with a broad range of organisms and cells. These include bacteria, lower eukaryotes, and cell cultures. However, in order to implement a genetic potentiation based screen, it is easier to work with a genetically manipulable organism. Among bacteria a large numbers of different species and strains are well-characterized and readily manipulable; among the lower eukaryotes the number is smaller. Nonetheless, several nonpathogenic fungi species are readily manipulable (e.g., *Saccharomyces cerevisiae, Schizosacharomyces pornbe, Neurospora crassa*). Most pathogenic fungi, however, are diploids (or of higher ploidy) rendering the isolation of large number of recessive mutations more difficult. Some pathogenic fungi such as *Candida glabrata* are haploid and could be used to isolate recessive mutations. *Candida glabrata* is closely related to *S. cerevisiae*. It is expected that the essential genes (as opposed to the pathogenesis genes) are most closely related between the two species. As it is expected that, in preferred embodiments, this method will focus on using essential gene products as drug targets (see below), the use of *C. glabrata* is not a major advantage.

Under these circumstances the wealth of information and the ease of genetic manipulation of *S. cerevisiae* currently outweighs the advantages of working directly with a pathogenic species. At least 700 thermosensitive mutants of *S. cerevisiae* have already been collected from various investigators in the field, indicating that a large mutant pool can be readily constructed from currently available strains. In addition, further mutants can be conveniently isolated by known methods.

The description of the methods herein emphasizes the use of *S. cerevisiae*, however, as indicated above, many other species and strains can also be used for particular screens. In particular, the method is readily adaptable to various bacteria, as the genetics of many bacterial species are reasonably well characterized or are being characterized.

B. Selection of Target Genes

A large variety of target genes can be used in the screening methods of this invention. In particular preferred embodiments, the target genes are essential genes. Essential genes can be defined as the genes whose deletion leads to a complete loss of viability on rich medium, such as on rich medium in a Petri dish. Use of such essential genes provides convenient detection of inhibitors active on these genes, as inhibition leads to growth rate reduction or growth arrest. The effects of inhibition of an essential gene may be static or cidal.

In addition to essential genes, other target genes may be utilized where the action of a modulator or inhibitor active on the gene leads to a change in growth rate.

III. Genetics

A. Mutagenesis: Types of mutants

Those skilled in the art are familiar with a variety of methods for generating mutants of microbial organisms or cells, for example chemical mutagenesis and UV light exposure among others, and for characterizing the mutants. Appropriate techniques are widely known and are available in numberous references, including, for example, Sambrook et al., MOLECULAR CLONING: A LABORATORY MANUAL 2nd ed., Cold Spring Harbor Laboratory Press, 1989. In addition, a large number of mutants have previously been prepared and are readily available. As described, a number of different types of mutants are useful as strains to be included in screening pools of the present invention.

In particular, two classes of mutants are readily obtainable and can provide the bases for two different and complementary types of genetic potentiation, however, the invention is not limited to the use of these classes. The first type of mutants are conditional lethal mutants. The most common class of these mutants are temperature sensitive mutants (ts mutants), which may be either heat or cold-sensitive mutants. The protein encoded by a ts mutant is inactive or unstable at a restrictive temperature, and often is also unstable at a lower temperature. Frequently the ts protein is also more sensitive to potential inhibitors, particularly at semi-permissive temperatures, but also often at permissive temperatures. This sensitization provides the basis for a first type of genetic potentiation.

While it is possible that this approach will identify some compounds that are specific for the mutated form of the protein and have no particular affinity for the WT protein, many compounds identified as active on the mutant form will also be active on the wild-type. In addition, the possibility of identifying compounds having activity only on the mutant form can be countered by isolating mutants of a second type. Strains are generated in which the expression of one essential gene is decreased (hypomorphs). This could be achieved by the construction of fusions between a weak promotor and the essential gene and introducing this construct into a strain that contains a deletion of the essential gene in question.

For *S. cerevisiae*, a more efficient method is to generate a collection of suppressible nonsense mutants in essential genes. Such a collection of hypomorphs can be generated using a method originally described by Riles and Olson, *Genetics* 118:601–607 (1988), which is incorporated herein by reference.

This method takes advantage of the sectoring phenotype of an ade2-101 suppressed by a sup11 gene present on an unstable plasmid. The plasmid carrying sup11 becomes essential for life if the strain acquires a sup11 suppressible nonsense mutation in an essential gene.

A strain carrying a wild type ade2 gene forms white colonies while a strain containing a nonsense ochre mutation in the ade2 gene (ade2-101) forms red colonies because it accumulates a pigmented intermediate in the adenine biosynthetic pathway. sup11 is an ochre suppressor tRNA mutation capable of suppressing (complementing) ade2-101. The resulting double mutant (ade2-101, sup11) forms white colonies. If the sup11 gene is carried on an unstable vector such as a centromeric plasmid (1% loss per generation) the strain forms sectored colonies (white sectoring to red).

That strain is mutagenized in order to create ochre suppressible mutations in essential genes. Strains containing ochre suppressible mutations in an essential gene will be easily recognized because sup11 must be present to allow expression of the essential gene. This results in a non-sectoring white colony.

Mutants of that type are potentiated because they contain a limiting amount of an essential protein. Naturally, the protein expressed in the presence of the suppressor contains a missense (Tyr in place of the stop codon in the case of sup11) but this is not the basis for the non-sectoring phenotype.

This approach can also be applied to other organisms for which unstable nonsense suppressors are available or are identified.

B. Number of Mutants for Screen Pool

The number of strains, e.g., conditional growth mutants, to include in a screening pool can vary depending on the tags being used and the available mehtods for discrimination. It can also vary depending on the number of appropriate strains which can be co-cultured. It can further depend on the numbers of stains useful or necessary to provide coverage of the relevant targets. For example, in the case of screens for inhibitors of essential genes in a particular organism, it is desireable to utilize a sufficient number of strains so that it is probable that each essential gene is represented in the pool (or at least each essential gene for which a mutant is obtainable). In cases in which the number of strains is large, e.g., hundreds or thousands, the strains can be screened in a single pool if the strains discrimination method being utilized is capable of identifying individual strains in such a large pool, or the set of strains can be divided into a number of smaller pools which can be screened separately.

Screening for compounds targeting essential genes in yeast illustrates the consideration of comprehensive target coverage. The number of essential functions in yeast is higher than in bacteria. Moreover a larger fraction of the compounds identified as antifungals will be toxic to mammalian cells. Therefore it is reasonable to screen a library of mutants larger than that which would be screened in the case of a bacterial species, such as *Staphylococcus aureus*.

Estimates of the number of essential genes in yeast vary and depend on the method used for the estimation. Estimates have been based on the number of complementation groups in libraries of ts mutants and nonsense suppressible mutants. Others have used random gene disruptions, and, finally, estimates have been based on the systematic disruption of all ORFs in some sequenced yeast chromosome. A systematic gene disruption effort for *S. cerevisiae* is currently in progress and 455 essential genes have been identified so far.

Based on this number of essential genes approximately 1000 ts mutants and/or 1000 hypomorphs would preferably be isolated. This number, approximately 2 times the number of essential genes, will provide a good coverage of essentially all essential functions. Mutants are preferably isolated in both mating types to facilitate the grouping of genes in complementation groups.

As indicated, in the case of most bacteria, the number of essential genes in smaller, e.g., 200–300, so that coverage of substantially all the essential gene targets in an organism would require appreciably fewer strains. In most cases, it is believed that one strain per essential gene would provide reasonably comprehensive coverage.

Clearly, however, much smaller pools of strains will also provide useful screening, both for essential gene screening and for other target types.

C. Assigning mutants to complementation groups

In working with large collections of mutants, it is helpful to eliminate duplicate strains in order to reduce the screening and analysis work. Some genes might mutate more frequently than others to the ts phenotype, for example, so that mutants of such a gene would be present in multiple versions following mutagenesis. Duplication can be eliminated using complementation tests between the strains. Complementation tests can be performed iteratively in order to eliminate mutants as quickly a possible. For essential genes, for example, the goal is to end up with one ts and/or one hypomorph or other appropriate mutant for each essential gene.

D. Identifying genes

Paradoxically, since the entire yeast genome is now sequenced, the fastest way to identify a mutation is to clone the gene that complements it. (This, is also true for a number of bacterial species.) Both phenotypes (ts and sectoring) can be complemented in one step: the ts mutant by transforming a library at restrictive temperature and the nonsectoring mutant by identifying a sectoring colony after transformation. One or two complementing clones can be recovered in *E. coli* and submitted to one sequencing run in order to identify the yeast genomic DNA present at the junction between vector and insert sequences. Sequencing of the vector/insert junctions of two independent plasmids should allow identification of the complementing gene in the majority of the cases.

For organisms for which a fully sequenced genome is not available, if it is desireable to identify the mutated gene, routine methods can be used to obtain the coding and/or genomic sequence of the gene. For example, complementing clones to specific mutnat strains can be identified from a cDNA library using appropriate expression vectors and the nucleic acid sequences encoding the complementing gene product can be sequenced from the corresponding cDNA inserts.

E. Characterization and Prioritization of Mutants and Target Genes

The characterization of the mutations obtained will provide useful information on the suitability of each corresponding gene product as a drug target. In order to maximize this information, several secondary phenotypes should preferably be determined for the entire collection, such as the tightness of each allele, the reversion rate, and lysis.

Tightness is significant because, if the strain displays a leaky ts phenotype, it probably means that in the absence of the product of that gene (high temperature) the strain takes several generations to arrest growth. That means that an inhibitor of that protein, even if it eliminates the activity of the protein instantly, is going to require the same length of time to arrest the growth the organism. This is a trivial phenotype to determine in the case of the ts mutants (simply monitor numbers of viable cells following a shift from permisive to non-permissive temperatures). For hypomorphs a secondary screen involving a suppressible canavanine resistant allele in the genetic background of the strain can address this question (see Riles and Olson, 1988, *Genetics* 118:601–607).

The reversion rate, in particular for the ts, is an important practical consideration for running the screen in semipermissive conditions. If the strain can revert from ts– to ts+ (through intra-or extra-genic reversion) it might also be able to become resistant to the inhibitor using the same mechanism.

Determining the extragenic reversion rate of the suppressible nonsense mutants is also very informative. It provides valuable information to prioritize the different genes. This can be done, for example, by plating on 5-FOA (sup11 is on a URA3 plasmid) and looking for red revertants.

A third phenotype that should be investigated is lysis. That can be done very simply by determining which mutants release their sequence tags in the culture medium in non-permissve conditions. This determination can use DNA arrays as described below. Lysis can be good or bad. On one hand if the strain lyses in nonpermissive conditions the inhibitor could cause the same effect. The inhibitor is therefore cidal, not static. One the other hand, if it causes lysis, a massive dose of foreign antigens may be released in the circulation system of an infected host organism, and that can cause treatment problems.

IV. Screen Construction

A. Mutant tagging

In preferred embodiments, each mutant will be individually tagged with a unique DNA sequence. Practically, that will simply require the construction of a library of plasmids each containing a different insert in a unique site of the vector. That site will be flanked by identical 20-mers in inverted orientation. That 20-mer is used to amplify all the inserts from the pooled population using a single-primer PCR reaction, thereby minimizing biases.

While, the single primer approach is suggested, other primer choices could also be used, e.g., using two different primers (and corresponding flanking sequences) and/or different lengths of primers. For example, one could simply clone the tags in any of the restriction sites of the polylinker of a pRS plasmid (Sikorski et al., 1989, *Genetics* 122:19–27) and use the universal primer and the reverse primer for the PCR amplification. The pRS plasmids all contain yeast selectable markers. They can be transformed in the various mutant strains using the Lithium Acetate transformation procedure (Ito et al. 1983, *J. Bacterial.* 153:163–168).

B. Using Pools of Strains: Strain Discrimination Assay

A growth assay is used to determine the antimicrobial effect of each compound. As a large number of mutants will be assayed in parallel, the tagged mutants will be pooled and their growth characteristics determined using DNA array technology or using another method of discriminating growth differences of the individual pooled strains.

1. ExoIII Method

Turning the negative signal (missing tag) into a positive one may be the most sensitive method, and essentially unlimited numbers of mutants could be pooled.

One way of achieving this is by using an exonuclease such as exoIII, which has significantly different digestion rates for specific types of dsDNA ends. In the case of exoIII, the enzyme is capable of degrading double stranded DNA starting from blunted or recessed 3' OH but not overhanging 3' OH ends. The method is shown schematically in FIG. 4. Other enzymes can be used similarly by matching the appropriate exonuclease activity to the type of overhang created by manipulation of the tag sequences.

Assuming a pool of 1000 tagged mutants is grown, one of which is sensitive to the tested chemical (mutant #1000, tagged with tag#1000. That strain would then be missing from the test pool if its growth is inhibited. The absence of a strain can be determined in the following way:

- all tags are PCR amplified after growth in the presence or the absence (control pool) of a test chemical
- the control pool is cut in the primer sequences with a restriction enzyme(e.g., KpnI in FIG. 4) that generates 3' overhangs (resistant to exoIII)
- both pools are mixed, denatured and reannealed.

This forms heterohybrids (one strand from each pool) and homohybrids.

- exoIII treatment. This will degrade all double stranded hybrids that contain either blunt or recessed 3' ends (#2,3,4 in the FIG. 4). Hybrid number 1 is resistant to exoIII. If during the annealing we use an excess of the test pool we can minimize the formation of Hybrid 1
- the only double stranded molecule completely resistant to exoIII should correspond to the tag that is absent in the test pool. In other words the sensitive DNA strands of the test pool target the control pool for degradation.

If a specific tag is missing in the test pool (#1000), its counterpart in the control can only form resistant homohybrids.

- separate the product of exoIII digestion and recover full length double stranded molecules (the tags missing from the test pool).

2. DNA Array Method

The general features of this method were indicated in the Overview section above.

All the tagged mutants and their wild type parents are pooled in a master stock. Samples of this stock are grown in the absence and the presence of each test compound. Total DNA is extracted. The sequence tags are recovered by PCR amplification and fluorescently labeled (other labels can also be used). Those probes will be hybridized to arrays of the tags in order to determine their representation in the original pool of cells.

DNA array methods have been described (in principle) in two recent publications (Shena et al., 1995, *Science* 270:467≧470; Hensel et al., 1995, *Science* 269:400–403) for use in other contexts.

Schena et al. described the use of arrays prepared from PCR amplified complementary DNAs (cDNAs). The arrays were printed on glass microscope slides. The probes were prepared by reverse transcription of mRNA from a particular plant. Hybridization of the probes to the array was performed under high stringency. This process indicated the expression level of the specific genes represented in the cDNA array.

Hensel et al. used arrays as part of a procedure to identify bacterial (*Salmonella typhimurium*) virulence (pathogenesis) genes active in a murine model of typhoid fever. The procedure utilized transposon insertion mutagenesis to tag bacteria with specific sequence tags. It was expected that some of the insertions would occur in genes important for infection, at least partially inactivating those genes. The mutants were then pooled and used to infect the mouse host. Insertions in virulence genes were identified by the absence (or reduced presence) of the mutant bearing a particular sequence tag following host infection. The presence or absence of a mutant was determined by the presence or absence of a particular tag in the pool of PCR amplified and labeled tags post-infection; this was determined by hybridizing the amplified pool to an array of DNA extracted from the pre-infection pool.

An additional description of the use of DNA arrays is provided in Shalon et al., 1996, *Genome Research* 6:639–645. This reference describes the use of two-color fluorescent probe differential hybridization on a DNA array using labeled isolated yeast chromosomes as probes to hybridize to an array of yeast genomic fragments.

Yet another description is in Shoemaker et al., 1996, *Nature Genetics* 14:450–456, which describes the use of a DNA array in the analysis of *S. cerevisiae* deletion mutants. The experiments used PCR amplification of 20-mer DNA molecular tags, hybridization of the amplification products to an array of complementary DNA sequences.

These references demonstrate that detection of DNA tags using hybridization on complementary arrays can be performed in a practical manner. A variety of different formats may be used, however, a method which provides a dense array is preferred for large scale screening. Such arrays can, for example, be constructed by printing the array pattern on glass slides, generally as described in Schena et al., but can also be constructed on other media.

V. Data Processing

Use of the DNA array technology will produce a large quantity of information. Both the amount of information and the identification of the relevant portions in it can beneficially utilize relational databases and neural network analysis.

VI. Pathogenic Fungi

In addition to screening directly against hypersensitive mutants of essential genes from a standard experimental microbe like *S. cerevisiae*, screening can be performed with homologs (homologous genes) from various other microbes, including other fungi. A good portion of those will be able to functionally complement. Next, the gene is potentiated. This can be done by hydroxylamine mutagenizing the complementing plasmid in vitro, and transforming back in a *S. cerevisiae* strain deleted for this gene. This method will identify ts alleles of the gene. By site directed mutagenesis it is even easier to generate a suppressible nonsense allele. Both types of alleles can be molecularly tagged and introduced into a strain pool.

The following steps describe one possible method, however, a variety of other methods and modifications can also be used.

1) A wild type copy of the essential gene is placed on a URA3 based CEN plasmid such as pRS316 (Sikorski et al., 1989, *Genetics* 122:19–27). That plasmid can be counterselected on fluoorotic acid containing medium (Boeke et al., 1987, *Meth. Enz.* 154:164–175).

2) The chromosomal copy of the essential gene is deleted (all these basic manipulations of yeast are described in Kaiser, Michaelis and Mitchell, Methods in Yeast Genetics, Cold Spring Harbor Laboratory Press, 1994).

3) A DNA library from a pathogen is transformed in this strain and the functional homolog of the *S. cerevisiae* essential gene is identified as a fluoorotic acid resistant transformant.

4) The pathogen's homolog is mutagenized by hydroxylamine and retransformed in *S. cerevisiae*. The transformants are screened for the desired phenotype (ts or hypomorph) using the procedures described above.

VII. Human Genetics

The method can also be extended to certain human genes. Some yeast genes are conserved all the way to humans. While these may not be good targets for antifungal agents, they could make useful anticancer drug targets. This again merely involves adding more strains in a strain pool (i.e., adding to the matrix).

Two examples of the use of genetic potentiation for human applications would be to screen for (1) inhibition of cell cycle progression (anticancer), by screening a *S. cerevisiae* cdc28 deletion mutant containing the potentiated human homolog (Lee and Nurse, 1987, *Nature* 327:31–35; Lee and Nurse, 1988, *Trends in Genetics* 4:287–290); (2) inhibition of cholesterol biosynthesis by using *S. cerevisiae* deleted for HMGCoA reductase genes (Basson et al., 1987, *Genetics* 117:645–655) and complemented by potentiated human homologs.

For both examples, as well as other genes, a ts mutant or a hypomorph of the human gene can be derived, tagged, and the strain included in the matrix.

VIII. Compounds to be Screenned

The screening method of the present invention is appropriate and useful for testing compounds from a variety of sources for possible activity. The initial screens can be performed using a diverse library of compounds, but the method is also suitable for a variety of other compound libraries. Such compound libraries can be combinatorial libraries, natural product libraries, or various small molecule libraries. In addition, compounds from commercial sources can be tested; this testing is particularly appropriate for commercially available analogs of identified compounds having activity in the screen. Preferably the methods described herein are used with small molecules, which preferably refers to compounds having a molecular weight of less than about 3000 daltons, more preferably less than about 2000 daltons, still more preferably less than about 1000 daltons, and most preferably less than about 600 daltons.

Once a compound having a desirable activity is identified, derivatives of that compound can be prepared and tested by medicinal chemistry using synthetic and testing methods known to those skilled in the art. Such derivatization can be used to optimize the characteristics of a potential therapeutic compound for activity, low toxicity, serum stability, and other relevant characteristics.

IX. Antimicrobial Agents

A. Pharmaceutical Applications

Compositions containing antimicrobial agents prepared by the method of this invention can be administered for prophylactic and/or therapeutic treatments. In therapeutic applications, the compositions are administered to a patient already suffering from an infection from a microbe, in an amount sufficient to cure or at least partially arrest the symptoms of the infection. An amount adequate to accomplish this is defined as a "therapeutically effective amount or dose." Amounts effective for this use will depend on the severity and course of the infection, previous therapy, the patient's health status and response to the drugs, and the judgment of the treating physician. In prophylactic applications, compositions containing the antimicrobial agents of the invention are administered to a patient susceptible to, or otherwise at risk of, a particular infection. Such an amount is defined to be a "prophylactically effective amount or dose." In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

B. Administration

Although it is possible to administer an agent produced from this invention alone, it is preferable to present it as part of a pharmaceutical composition containing the active compound and a carrier or excipient.

The formulations of the present invention preferably contain at least one antimicrobial agent and one or more pharmaceutically or therapeutically acceptable carriers or excipients. The antimicrobial agent is in such amount as to constitute a pharmaceutically or therapeutically effective dose or amount. The compounds can be prepared as pharmaceutically acceptable salts (i.e., non-toxic salts which do not prevent the compound from exerting its effect).

Carriers or excipient can be used to facilitate administration of the compound, for example, to increase the solubility of the compound. Solid carriers include, e.g., starch, lactose, dicalcium phosphate, microcrystalline cellulose, sucrose, and kaolin, and optionally other therapeutic ingredients. Liquid carriers include, e.g., sterile water, saline, buffers, polyethylene glycols, non-ionic surfactants, and edible oils such as corn, peanut and sesame oils, and other compounds described e.g., in the MERCK INDEX, Merck & Co., Rahway, N.J. In addition, various adjuvants such as are commonly used in the art may be included. For example: flavoring agents, coloring agents, preservatives, and antioxidants, e.g., vitamin E, ascorbic acid, BHT and BHA. Various other considerations are described, e.g., in Gilman et al. (eds) (1990) Goodman and Gilman's: *The Pharmacological Basis of Therapeutics*, 8th Ed., Pergamon Press. Methods for administration are discussed therein, e.g., for oral, intravenous, intraperitoneal, or intramuscular administration, subcutaneous, topically, and others. Generally, preferred routes of administration are intravenous and intramuscular.

These pharmaceutical compositions can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. For some compounds a pharmacologically acceptable salt of the compound will be used to simplify preparation of the composition. Preferred salts include sodium, potassium, arginine, glycine, alanine, threonine. These are prepared, preferably, in water suitably mixed with a surfactant such as hydroxypropylcellulose.

X. Monitoring the Fate of Strians in A Growth Environment

Strains having distinguishable tags can be used in a growth environment, particularly in an in vivo environment, and the fate of one or more individual strains in a pool of strains monitored. Use of the tagging and detection methods described above allows convenient and efficient determination of the response of one or more of the strains in a pool to the particular environmental conditions. In these strains, a tag, such as a nucleic acid sequence tag, is not placed in a location in the cells of the strains such that the presence of the tag itself significantly affects the fate (e.g., growth) of a strain in the growth environment. Thus, a tag is preferably not placed in a location which affects the activity of an essential gene, or, in the case of in vivo application, in a pathogenesis gene. In this method, a pool of tagged strains is placed in the particular growth environment, and the presence of one or more of the strains in a sample(s) recovered from the environment is determined. Change in the presence of a strain is indicative of the response of the strain to the environment. In preferred embodiments, the strains, tags, and methods for determining the presence of the strains are as described above for the screening methods. In particular, the tags are preferably distinguishable nucleic acid sequence tags, including tags differing in length and specific sequence tags. Also in preferred embodiments, the growth environment is an in vivo environment in a multi-cellular organism, e.g., a vertebrate organism such as a mammal.

This method provides compound evaluation in an animal-sparing and compound-sparing manner. In preferred embodiments the method involves evaluation of the effects of an inhibitor compound on a plurality of strains in vivo. Thus, for example, an animal, such as a mammal, can be used in an infection model as an indication of the effects of treatment with a previously identified inhibitor compound. The use of the infection model can encompass evaluation of the effects of the compound with different routes of administration and/or the effects on a number of different isolates of a single microbial organism. Alternatively, a mix of different microbial species may be pooled, which may include more than one isolate of one or more of the species. In addition, both natural and artificially generated mutants can be used.

As currently practiced, evaluation of a compound would involve the use of separate sets of animals for each of the strains against which the compound is to be evaluated. Thus, the present method provides efficiency both as to the amount of compound which is required to perform the evaluations (compound availability is often limited) and as to the number of animals which will be required for testing. This method is particularly useful in the testing of compounds against species of organism which are known from clinical isolates to have significant variation in susceptibility to some inhibitors. An example of such an organism is *Staphyloccus aureus*. A large number of clinical isolates have been observed which have widely varying susceptibilities to various classes of antibiotics, including β-lactams.

A variety of infection models are known to those skilled in the art, in particular, infection models which are correlated with physiological or therapeutic effects in humans are known and widely used. Such models can be used in the present method; those skilled in the art understand the selection of models appropriate for use with particular microbes and types of compounds. Non-limiting examples of infection models which may be used, particularly for bacterial infections, are a rat peritoneal implant chamber model, intramuscular and subdermal abscess models, neutropenic thigh model, DBA/2 pyelonephritis model (target organ:kidney assay=TOKA), and an intraperitoneal catheter placement model.

Preferably the method also uses at least one control, in which no inhibitor is administered. Disappearance or reduction of the presence of a strain from the test organism but not from the control indicates that the inhibitor is active against that strain in the particular in vivo environment and or by the particular mode of administration.

For evaluation of the efficacy of particular compounds in vivo, a pool of tagged strains is introduced into a test animal which is selected to be suitable for the microbial strains in the pool and the compound or formulation or pharmaceutical composition to be tested. Preferably a control animal is also used. It is also advantageous in order to obtain reliable results to use more than one test animal. For the test animal, an inhibitor is administered to the animal. The mode of administration will vary for different animals and infections models and inhibitors. Those skilled in the art will understand the appropriate choices; in addition, the method can be used to evaluate different administration modes for the same compound.

Following administration of the inhibitor, one or more samples are taken from the animal or animals. The sample locations are selected such that the samples are expected to contain microbes from the pool if those microbes are still present in the organism. In general for nucleic acid sequence tags, nucleic acid, e.g., DNA, from the pool microbes (which may be mixed from nucleic acid from the host animal) is retrieved and the tag sequences are amplified using PCR. The presence of a particular tag in the amplified tags thus indicates the presence of the strain having that tag in the animal. The use of the control animal serves to indicate that a change in the presence of a strain in a test animal is due to the administration of the inhibitor if the change in presence is observed only or to a significantly greater degree in the test animal than in the control animal.

Detection of nucleic acid sequence tags can be performed as described above. In particular, the tags can be detected and distinguished using electrophoresis of amplified tags in the case where the tags differ in length. The tags can likewise be detected and distinguished using nucleic acid probe hybridization in the case where the tags differ in nucleotide sequence, i.e., are specific sequence tags.

XI. EXAMPLES

Example 1

Strains Respond Similarly to Inhibitors Whether They are Treated Individually or in Pools.

Biologically this is an important experiment, demonstrating that the results obtained in pools mimic the results we would have obtained had we analyzed the strains individually. We had previously determined that strains 1153 and 1138 are hypersusceptible to the compounds designated MC-225269 and MC-206854 respectively. Minimum inhibitory concentrations (MIC) for these 2 compounds and for 3 other compounds for which none of the strains were hypersensitive were determined on the mutant strain and six other, not hypersusceptible strains (shown in Table 1 below). Growth of the pooled strains was conducted at concentrations of the inhibitors which were above the MICs of the sensitive strains (approximately 2× the MIC) and below the MICs of the non-sensitive strains.

TABLE 1

| Strain | | Ampho B | 5FCyt | MC206854 | MC225269 | 4-NQO |
|---|---|---|---|---|---|---|
| | | \multicolumn{5}{c}{MIC 40 hr after growth at 30° C. (μg/ml, or mM for 4-NQO)} | | | | |
| 1138 | Lys+ | 4 | 32 | 64 | ≦0.25 | 4 |
| 1153 | Lys+ | 8 | 64 | 4 | 32 | 4 |
| YP102 | Lys− | 2 | 8 | 128 | 8 | 2 |
| YP5 | Lys− | 2 | 8 | 64 | 8 | 1 |
| F761 | Lys− | 2 | 16 | 64 | 4 | 1 |
| 461 | Lys− | 2 | 4 | 32 | 8 | 2 |
| 462 | Lys− | 2 | 8 | 128 | 16 | 2 |
| 463 | Lys− | 1 | 16 | 32 | 8 | 4 |
| | | | | Tested at 8 μg/ml in pool | Tested at 0.5 μg/ml in pool | |

The two hypersusceptible strains are lysine prototrophs (Lys+), all six other strains are lysine auxotrophs (Lys−). Two pools, of seven strains, each containing one of the hypersusceptible Lys+ strains and the six Lys− strains were exposed to individual compounds causing selective inhibitions. The concentration of the compounds in this experiment was about 2 times the MIC concentration of the susceptible strain. At this concentration the susceptible strain, but none of the other six strains, would be inhibited. Both pools were incubated at 30° C. in the presence and the absence of compound.

Figure 5A:
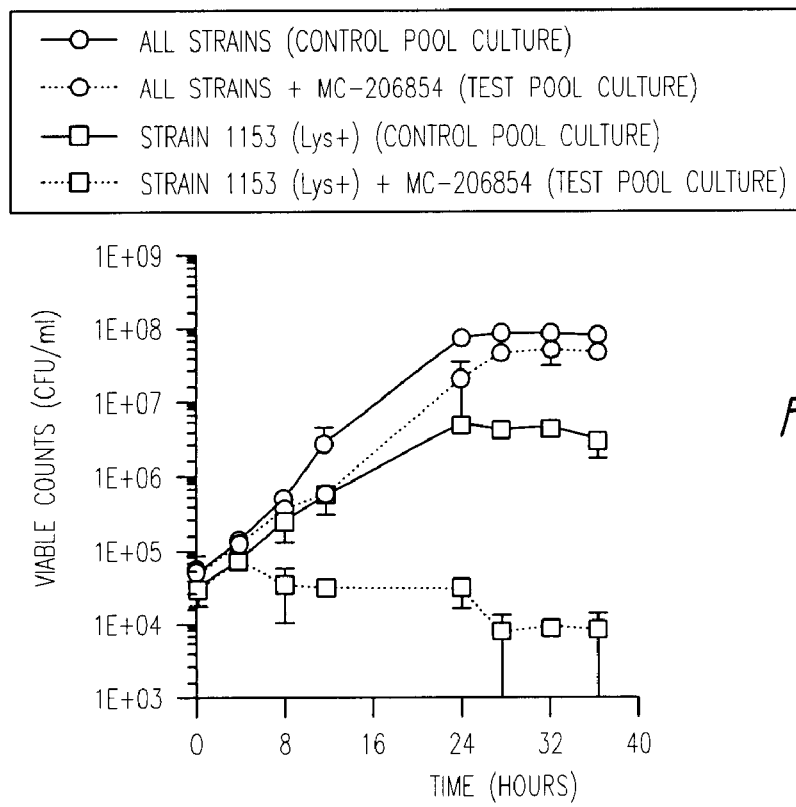
FIGS. 5A and 5B are graphs showing the results of inhibition of two strains of *S. cerevisiae* in pools of 7 strains by two compounds. In 5A, the compound exerts a cidal effect on the sensitive strain because the number of that strain present in the pool following growth are less than the numbers present early in the incubation.
Figure 5B:
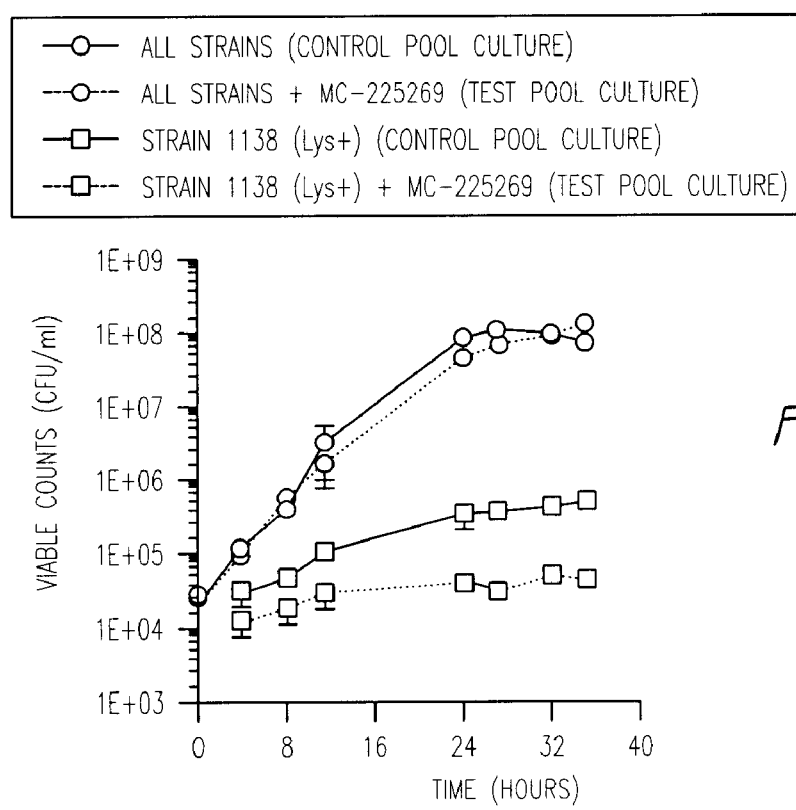

The representation of the susceptible strain was estimated at various time points by plating on selective media and determining the numbers of colonies able to grow under the selective conditions. Estimates were performed in duplicate at every time point. The results are shown graphically in FIG. 5A and B.

This experiment provided several answers to typical concerns about multiplexing:

Strains in pools do indeed grow to the expected saturation (approx. $10^8$ cfu/ml);

The effect of a specific inhibitor against a specific strain in pools can be detected and measured through genetic markers; the effect could also be detected through the use of sequence tags as a mean to identify individual strains;

There was no rescue or cross-talk between wild type and hypersusceptible mutants in these experimental pools;

Individual strains in a pool do not necessarily maintain their initial inoculum proportion due to their different growth rates. However, growth rates for individual strains were highly reproducible (see Example 2 for more data on this point);

Having a reproducible slow growth rate is not necessarily a problem for multiplexing so long as differences can be detected between control and test cultures (e.g., 10-fold). This is exemplified by strain 1138, which is depleted by growth in the pool even without an inhibitor compound. However, even in this case, a clear difference is observed in the presence of the inhibitor compound. Growth to saturation (plateau) allows the recording of the maximal differences between control and test cultures. This is a practical advantage of using pools rather than individual cultures. If a strain is only partially inhibited (slower growth rate) by a compound it will often ultimately reach a similar optic density. Therefore, when measured individually, the signal (OD of control minus OD of mutant) passes through a maximum and subsequently disappears. When measured in pools this difference increases until the pool reaches saturation ($1-2\times10^8$ cfu/ml). After that point the entire culture stops growing because some nutrients have been exhausted. If the measurement is done after the pool reaches saturation, one records the maximum difference possible between the test strain and the control.

Example 2

Strains Grow Reproducibly in Pools.

In preferred embodiments, the effect of a compound on each strain in a pool is detected through a differential hybridization. It is therefore important that the representation of each strain in the pool be reproducible. Note that it is not critical that each strain grow at the same rate.

In order to establish that individual strains grow reproducibly, we generated a pool of 51 strains. This pool is composed of 50 different ts mutants to which is added a test strain. This test strain carries yet another ts mutation and the ura3-52 mutation conferring resistance to 5-fluoroorotic acid (5FOA).

A master stock is generated in which each strain is seeded equally (approximately 2% each). That stock is then inoculated and grown repeatedly to saturation. In the end of the growth period the representation of the test strain in the pool is measured by calculating the ratio of 5FOA resistant to 5FOA sensitive cells.

Results are described for three independent cultures. Each culture was measured in triplicate. The final representations in the three cultures were 7.8±1.9%, 6.7±0.84%, and 7.2±2.1%. This experiment shows that this test strain consistently and reproducibly grows faster then the average of the pool. Its representation at the end of the growth period is 6 to 7% while it was seeded at 2%. More importantly, if we estimate the variability of the growth of this test strain from culture to culture by calculating the mean and sd of the three independent measurements we obtain 7.2+/−0.55%. This variability is smaller than the error associated with the measurement of the 5FOA resistance in each culture. The same experiment was performed using five other test strains. The growth of these five test strains was equally reproducible. As expected, all strains tested have a different growth rate and consequently their representation in the pools at the end of the growth period ranges from 0.2% to 20%.

Example 3

Hybridizations Using PCR Generated Mixed Probes Detect Known Differences in Amounts of DNA.

The multiplex method of this invention reduces the problem of determining cell numbers to that of quantitating various DNA sequences in pools. We modeled this experiment by demonstrating that DNA hybridization can detect known differences in pools of tags. For this experiment the pools are in the form of plasmid mixes.

Figure 7:
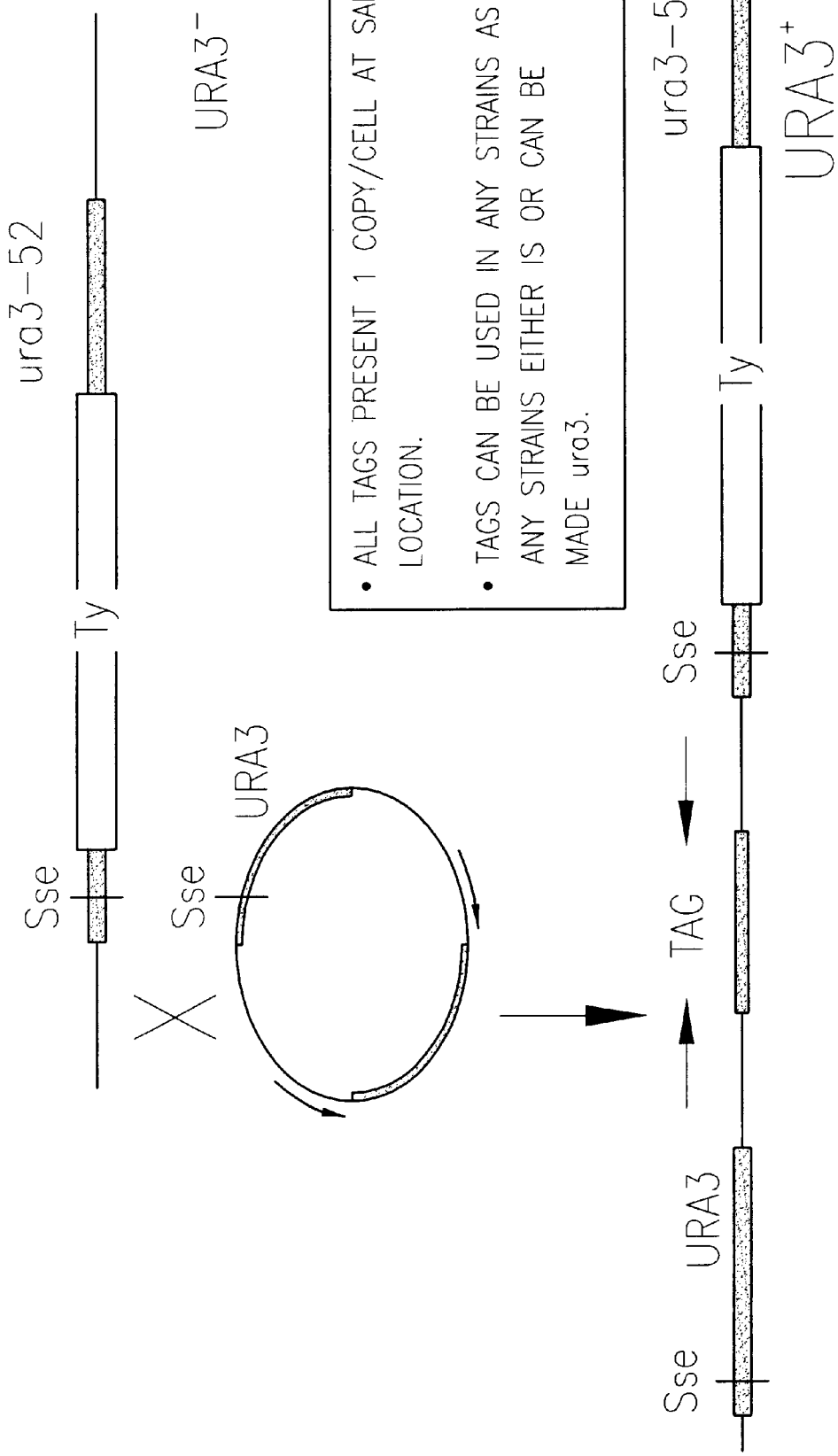
FIG. 7 is a schematic illustration of a method for generating *S. cerevisiae* strains having recombinant DNA tags inserted in a chromosome in single copy. The tag will be inserted at the same location in each strain. In this case the tag is inserted in the ura3 locus.

Tag generation: A collection of sequence tags was generated in the following manner. 500–600 bp SacI and KpnI restricted total DNA from salmon sperm was cloned in the polylinker of a pRS306. We identified a subset of these plasmids whose inserts do not cross-hybridize by performing Southern hybridization analyses. Each candidate sequence tag was used to probe a blot comprised of sequences complementary to several individual tags, including the tag serving as probe. Probes which only self-hybridized were considered unique and retained for future use. In those cases where a probe hybridized to $\geq 1$ sequence tag, one representative was retained, and the remainder eliminated from the tag pool. All these plasmids can be integrated in the yeast genome at the URA3 locus as shown in FIG. 7. Ten of these plasmids were used for the following experiment.

A. Plasmid Pool: DNA Quantitation Using Mixed Probe Hybridizations:

We generated pools of 10 non-cross-hybridizing tags in which the representation of one tag (#9) relative to the rest of the pool was varied. All pools contain a total of approximately 30 pg of tag-containing plasmids. In the first pool all plasmids are represented in a 1/1 ratio (i.e. 3 pg each). In the next three pools the amount of tag #9 is decreased by a factor of 10, 100 and 1000 (i.e. 300, 30, and 3 fg respectively).

A mixed probe was generated by PCR from each of these pools. The universal and reverse sequencing primers were used. PCR conditions were as follows: 94° for 1 min followed by 20 cycles of 940 for 30 sec, 53° for 30 sec, 72° for 1 min, followed by 3 min at 72°. Fluorescein 12-dCTP was incorporated during amplification.

Figure 6:
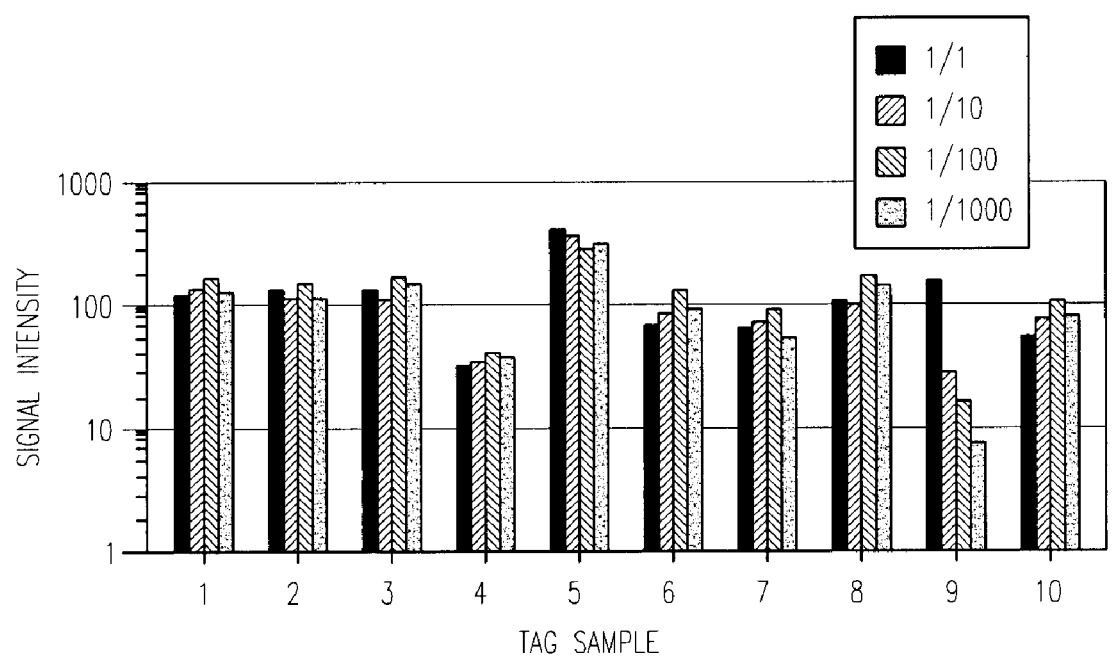
FIG. 6 is a bar graph showing that differences in the representation of a DNA sequence tag in a pool of tags can be detected using hybridization of mixed probes to specific tag DNA sequences. Specific tag-probe hybridization was detected following PCR amplification from the tags in a mixture of 10 tag-containing plamids. The reduction in concentration of sample 9 (tag 9) is clearly shown, with each factor of 10 reduction clearly etectable.

The four probes were hybridized to four identical dot blots composed of the 10 tag-containing plasmid inserts spotted on a GENESCREEN™ membrane. 10 ng of each insert was spotted. Detection of the hybridization signal using anti-fluorescein antibody was performed according to the "RENAISSANCE™" (Dupont). The results of this hybridization were visible by inspection and showed that differences in tag #9 representation are clearly detected. We also quantitated the hybridization signal using a phosphorimager. The bar graph shows that only the representation of #9 decreased with decreasing representation of the plasmid containing tag #9 in the plasmid pool (see FIG. 6).

Figure 8:
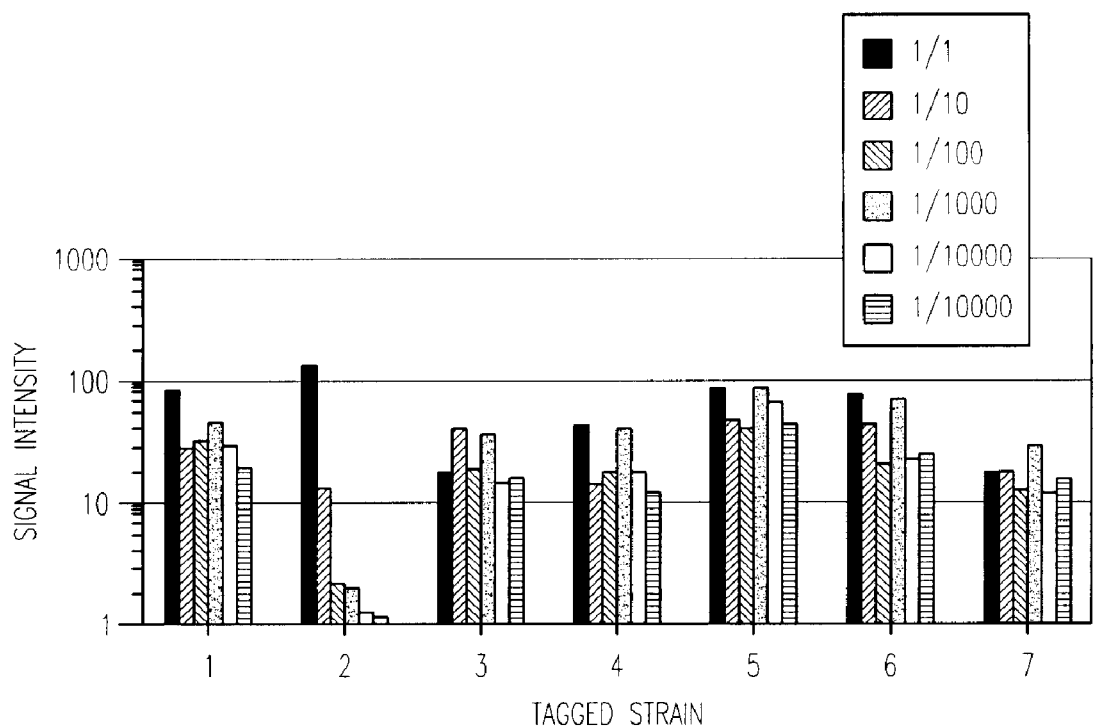
FIG. 8 shows a bar graph demonstrating that representation of a chromosomally integrated tag in a pool of tagged strains can be detected using hybridization of mixed probes to specific tag DNA sequences on a blot. Specific tag-probe hybridization was detected following PCR amplification from the tags in a mixture of 7 tag-containing *S. cereviae* strains. The reduction in concentration of the tagged strain #2 (the titrated strain) is clearly shown.

B. Mixed-tag Strain Pool: DNA Quantitation Using Probes Generated from Pools of Mixed Tagged Cells Seven strains were tagged using plasmids whose inserts do not cross-hybridize. Six pools of cells were generated, each containing approximately $7 \times 10^8$ cells. In pool one, all seven strains were represented in a 1:1 ratio ($1 \times 10^8$ cells each). In the next five pools, the amount of tagged strain #2 was diluted by a factor of 10 ($1 \times 10^7$ cells), 100 ($1 \times 10^6$ cells), 1000 ($1 \times 10^5$ cells), 10,000 ($1 \times 10^4$ cells), and 100,000 ($1 \times 10^3$ cells). Total genomic DNA was isolated from each pool using the Qiagen 20/G GENOMIC TIP™. 100 ng of genomic DNA from each preparation served a a template for PCR amplification. A mixed probe was generated using the M13 universal forward and reverse primers in a PCR reaction with the following cycling conditions: 95° C. for 1 min., followed by 25 cycles of 94° C. for 30 sec., 53° C. for 1 min., 72° C. for 2 min., followed by 5 min. at 72° C. Fluorescein 12-dCTP was incorporated during amplification. The six probes were hybridized to six identical dot blots composed of the 7 tag DNA fragments spotted on a GENESCREEN™ membrane. 10 ng of each fragment was spotted. Detection of the hybridization signal using anti-fluorescein antibody was performed according to the "RENAISSANCE™" (DuPont). The results of this hybridization show that differences in the tag #2 hybridization signal parallels the difference in the number of tagged strain #2 cells present in the mixed pools used for probe generation (FIG. 8).

Figure 9:
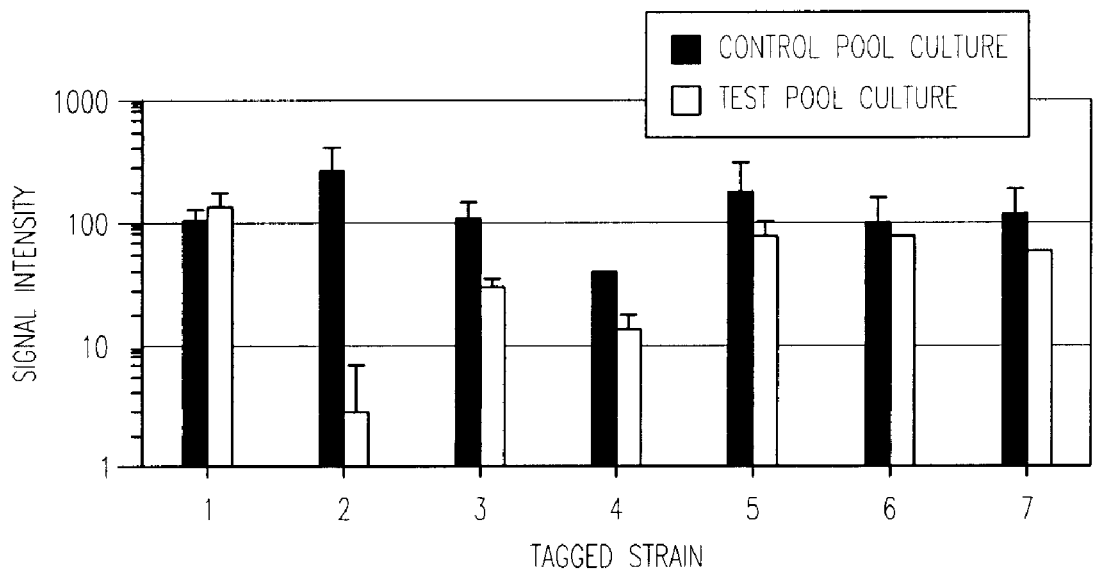
FIG. 9 is a bar graph showing the results of a replicate of the experiment reported in FIG. 5A, except that all of the strains in this pool were tagged ;and could be detected using hybridization of mixed porbes to specific tag DNA sequences on a blot. Specific tag-probe hybridization was detected following PCR amplification from the tags in a culture of 7 tag-containing *S. cereviae* strains after 36 hours of incubation with (test pool culture) or without (control pool culture) the presence of compound MC-206854. This compound preferentially inhibits strain 1153 (tagged strain #2 on the bar graph). Results demonstrate that strain 1153 is no longer detectable in significant amount when grown in a pool of strains in the presence of the inhibitor. This also correlates with the growth curves recorded for that strain as evaluated after cultivation of aliquots on selective plates during growth (FIG. 10 and similarly FIG. 5A).
Figure 10:
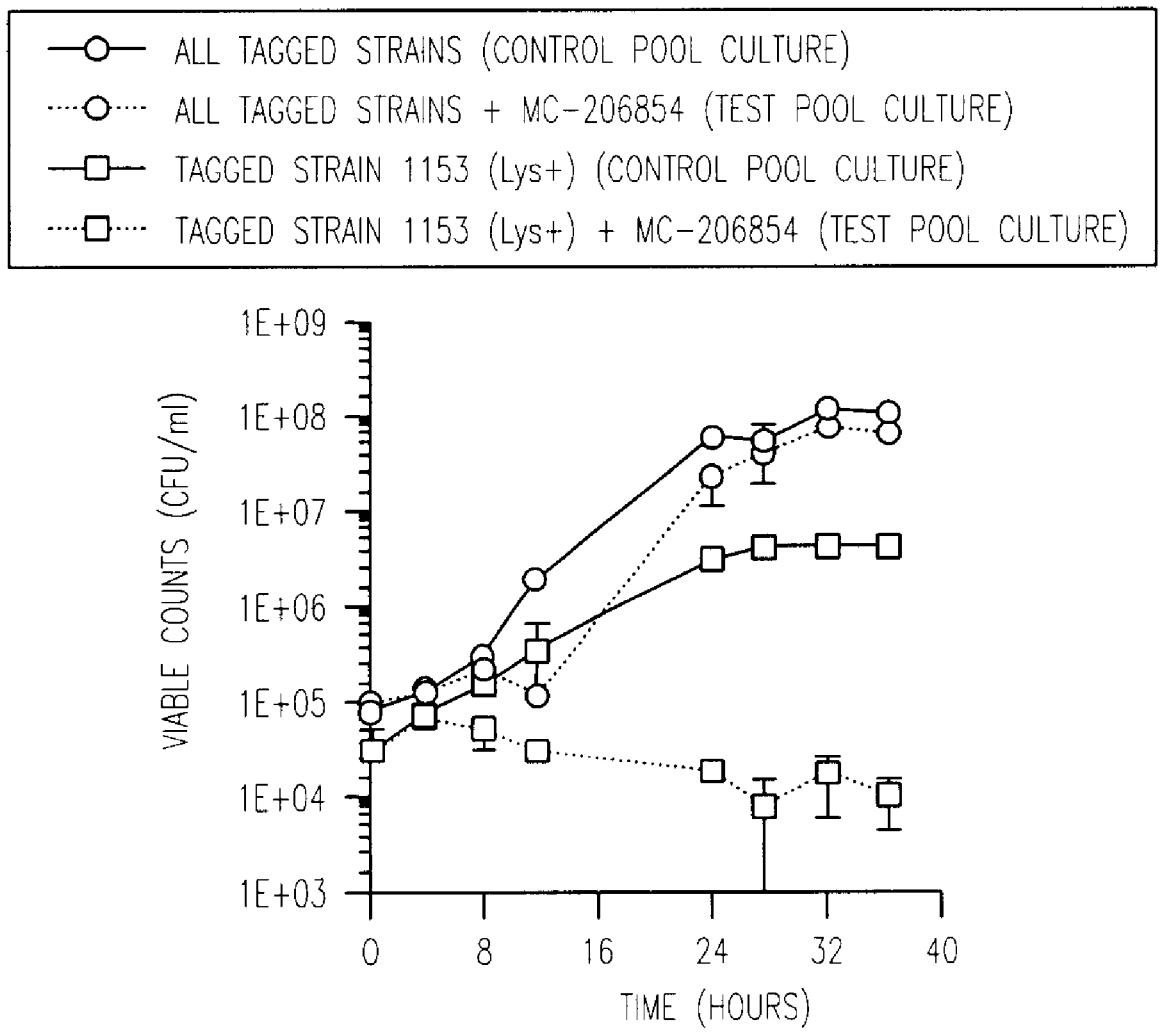
FIG. 10 is a graph showing growth curves of sequence tagged strains determined by plating aliquots of the cultures described in FIG. 9 on selective plates at different time points. Growth of strain *S. cerevisiae* 1153 (Lys$^+$) was specifically monitored using lysine-deficient plates. The observed killing of strain 1153 in the presence of compound MC-206854 was a reproducible event (see FIG. 5A), and in the present case was correlated with the specific tag-probe hybridization results (FIG. 9).

C. Mixed Tag Strain Pool: Detecting the Effect of an Inhibitor Against a Specific Strain The pooling experiment containing strain 1153 that was described in Example 1 was repeated using DNA sequence tagged derivatives of the same strains. The representation of the susceptible strain in the presence or absence of inhibitor compound was estimated at various time points by plating on selective media, as described above. At the final time point, cells were harvested and genomic DNA isolated from the treated and untreated pools, using the Qiagen 20/G GENOMIC TIP™ kit. 100 ng of genomic DNA was used as template for PCR amplification, as described in B. above. Four probes, corresponding to duplicates of treated and untreated cells, were used to probed four identical blots comprised of the tag DNA fragments corresponding to the 7 tags integrated in the strains. Hybridization results clearly demonstrate the reduction in signal intensity for the tag corresponding to strain 1153 (tag #2) in the treated pools as compared to the non-treated control pool. Results of two of the dot blots are shown in FIG. 9 where quantitation of hybridization is reported in a bar graph. These results parallel the results obtained when monitoring strain reduction by plating on selective media, demonstrating that the DNA sequence tag hybridiation approach accurately reflects the results obtained by genetic methods (FIG. 10), with greater potential to monitor the fate of individual strains within a large pool more easily.

The embodiments and methods described herein are not intended to be limiting to the invention. Those skilled in the art will recognize that the creation and analysis of pools of strains can be carried out in a similar manner using other techniques, and can be performed using any of a large number of different strains or species of microbes or cells. Such additional methods and uses are also within the breadth of the claims. Thus, other embodiments are within the following claims.

What we claim is:

1. A method of screening a plurality of test compounds for a test compound that decreases or increases the proliferation of a strain in a pool of strains, comprising:

providing a pool of strains, each strain differing from each other strain in a sequence of at least one gene, wherein each strain further comprises a distinguishable nucleic acid sequence tag, wherein each tag is distinct from the gene in that strain;

culturing the pool of strains in the presence of each test compound of the plurality of test compounds; and, determining whether the presence of the test compound decreases or increases the representation of a distinguishable nucleic acid sequence tag, wherein a decrease in the representation of a distinguishable nucleic acid sequence tag indicates a decrease in the representation of a tagged strain and a decrease in the representation of a tagged strain indicates that the test compound decreases the proliferation of that strain, and an increase in the representation of a distinguishable nucleic acid sequence tag indicates an increase in the representation of a tagged strain and an increase in the representation of a tagged strain indicates that the test compound increases the proliferation of that strain.

2. The method of claim 1, wherein the pool of strains comprises prokaryotic cells.

3. The method of claim 1, wherein at least one nucleic acid sequence tag comprises a recombinant DNA tag.

4. The method of claim 1, wherein each distinguishable nucleic acid sequence tag differs in length.

5. The method of claim 1, further comprising:

providing a control pool of strains; and culturing the control pool in the absence of the test compound;

wherein determining whether the test compound decreases or increases the representation of the distinguishable nucleic acid sence tag comprises comparing the representation of the tag in the pool of strains with that in the control pool.

6. The method of claim 1, wherein the pool of strains comprises a plurality of fungal strains.

7. The method of claim 1, wherein the plurality of test compounds comprises hundreds of test compounds or more.

8. The method of claim 1, wherein the plurality of test compounds comprises thousands of test compounds or more.

9. The method of claim 1, wherein the pool of strains comprises eukaryotic cells.

10. The method of claim 9, wherein the eukaryotic cells comprise yeast cells.

11. The method of claim 9, wherein the eukaryotic cells comprise human cells.

12. The method of claim 1, wherein determining the representation of a distinguishable nucleic awid sequence tag comprises hybridizing a complementary probe to the nucleic acid sequence tag.

13. The method of claim 12, wherein the complementary probe comprises a label.

14. The method of claim 13, wherein the label comprises a fluorescent moiety.

15. A method of screening a plurality of test compounds for a test compound that decreases or increases the proliferation of a strain in a pool of strains, comprising:

providing a pool of strains, wherein each strain differs from each other strain in a sequence of at least one essential gene, each strain further comprising a distinguishable nucleic acid sequence tag, wherein the tag is distinct from the essential gene in that strain;

culturing the pool of strains in the presence of each test compound of the plurality of test compounds;

determining whether the presence of the test compound decreases or increases the representation of a distinguishable nucleic acid sequence tag; and, correlating the distinguishable nucleic acid sequence tag, whose representation decreases or increases, with a tagged strain;

wherein a decrease in the representation of a distinguishable nucleic acid sequence tag indicates a decrease in the representation of a tagged strain and a decrease in the representation of a tagged strain indicates that the test compound decreases the proliferation of that strain, and an increase in the representation of a distinguishable nucleic acid sequence tag indicates an increase in the representation of a tagged strain and an increase in the representation of a tagged strain indicates that the test compound increases the proliferation of that strain.

16. The method of claim 15, wherein the compound has an effect on the essential gene.

17. The method of claim 15, wherein the test compound has an effect on an expression product of the essential gene.

18. The method of claim 15 wherein 15, the pool of strains comprises prokaryotic cells.

19. The method of claim 15, wherein at least one nucleic acid sequence tag comprises a recombinant DNA tag.

20. The method of claim wherein 15, each distinguishable nucleic acid sequence tag differs in length.

21. The method of claim 15, further comprising:

providing a control pool of strains; and, culturing the control pool in the absence of the test compound;

wherein determining whether the presence of the test compound decreases or increases the representation of the distinguishable nucleic acid sequence tag comprises comparing the representation of the tag in the pool of strains with that in the control pool.

22. The method of claim 15, wherein each distinguishable nucleic acid sequence tag comprises a recombinant DNA tag;

determining whether the presence of the test compound decreases or increases the representation of a distinguishable nucleic acid sequence tag comprises:

amplifying each recombinant DNA tag from a pool of strains cultured in the presence, and from a pool of strains cultured in the absence, of the test compound;

digesting each amplified recombinant DNA tag from the pool of strains cultured in the absence of the test compound with a restriction endonuclease that cuts the tags in a primer region leaving a 3' overhang;

mixing, denaturing, and reannealing each of the amplified DNA tags from the pools of strains cultured in the presence, and each amplified DNA tag cultured in the absence, of the test compound; and, digesting the mixture with an exonuclease, which does not digest dsDNA from an end having a 3' overhang.

23. The method of claim 15, wherein the pool of strains comprises eukaryotic cells.

24. The method of claim 23, wherein the eukaryotic cells comprise human cells.

25. The method of claim 15, wherein determining the representation of a distinguishable nucleic acid sequence tag comprises hybridizing a complementary probe to the nucleic acid sequence tag.

26. The method of claim 25, wherein the complementary probe comprises a label.

27. The method of claim wherein 26, the label comprises a fluorescent moiety.

28. The method of claim 15, wherein the pool of strains further comprises a strain or strains having a wild type allele corresponding to the essential gene in each strain of the pool of strains, and the wild type allele is labeled with a distinguishable DNA tag.

29. The method of claim 28, wherein the distinguishable DNA tag is a distinguishable recombinant DNA tag.

30. The method of claim 15, wherein the distinguishable nucleic acid sequence tag is a distinguishable recombinant DNA tag;

each distinguishable recombinant DNA tag is amplified after culturing of the pool of strains; and, determining whether the presence of the test compound decreases or increases the representation of a distinguishable recombinant DNA tag comprises hybridizing each amplified DNA tag in the pool of strains to an oligonucleotide array comprising a set of nucleotide sequences complementary to each distinguishable recombinant DNA tag; and determining whether the representation of a strain is decreased or increased by determining whether the representation of a distinguishable recombinant DNA tag corresponding to that strain is decreased or increased in the presence of the test compound compared to in the absence of the test compound.

31. The method of claim 22, wherein the distinguishable recombinant DNA tag are amplified by polymerase chain reaction amplification.

32. A method of screening a plurality of test compounds for a test compound that decreases or increases the proliferation of a strain, comprising:

providing a pool of strains, wherein each strain comprises a different variant within a species of an organism, each strain further comprising a distinguishable nucleic acid sequence tag;

culturing the pool of strains in the presence of each test compound of the plurality of test compounds;

determining whether the presence of the test compound decreases or increases the representation of a distinguishable nucleic acid sequence tag; and, correlating the distinguishable nucleic acid sequence tag, whose representation decreases or increases, with a tagged strain;

wherein a decrease in the representation of a distinguishable nucleic acid sequence tag indicates a decrease in the representation of a tagged strain and a decrease in the representation of a tagged strain indicates that the test compound decreases the proliferation of that strain, and an increase in the representation of a distinguishable nucleic acid sequence tag indicates an increase in the representation of a tagged strain and an increase in the representation of a tagged strain indicates that the test compound increases the proliferation of that strain.

33. The method of claim 32, wherein the pool of strains comprises prokaryotic cells.

34. The method of claim 32, wherein at least one nucleic acid sequence tag comprises a recombinant DNA tag.

35. The method of claim 32, wherein each distinguishable nucleic acid sequence tag differs in length.

36. The method of claim 32, further comprising:

providing a control pool of strains; and culturing the control pool in the absence of the test compound;

wherein determining whether the presence of the test compound decreases or increases the representation of a distinguishable nucleic acid sequence tag comprises comparing the representation of the tag in the pool of strains with that in the control pool.

37. The method of claim 32, wherein the pool of strains comprises eukaryotic cells.

38. The method of claim 37, wherein the eukaryotic cells comprise yeast cells.

39. The method of claim 37, wherein the eukaryotic cells comprise human cells.

40. The method of claim 32, wherein determining the representation of a distinguishable nucleic acid sequence tag comprises hybridizing a complementary probe to the tag.

41. The method of claim 40, wherein the complementary probe comprises a label.

42. The method of claim 41, wherein the label comprises a fluorescent moiety.

43. A method of screening a plurality of test compounds for a test compound that decreases or increases the proliferation of a strain, comprising:

providing a pool of strains, wherein each strain comprises a different microorganism, each strain further comprising a distinguishable nucleic acid sequence tag;

culturing the pool of strains in the presence of each test compound of the plurality of test compounds;

determining whether the presence of the test compound decreases or increases the representation of a distinguishable nucleic acid sequence tag; and, correlating a distinguishable nucleic acid sequence tag, whose representation decreases or increases, with a tagged strain;

wherein a decrease in the representation of a distinguishable nucleic acid sequence tag indicates a decrease in the representation of a tagged strain and a decrease in the representation of a tagged strain indicates that the test compound decreases the proliferation of that strain, and an increase in the representation of a distinguishable nucleic acid sequence tag indicates an increase in the representation of a tagged strain and an increase in the representation of a tagged strain indicates that the test compound increases the proliferation of that strain.

44. The method of claim 43, wherein the pool of strains comprises prokaryotic cells.

45. The method of claim 43, wherein at least one nucleic acid sequence tag comprises a recombinant DNA tag.

46. The method of claim 43, wherein each distinguishable nucleic acid sequence tag differs in length.

47. The method of claim 43, further comprising:

providing a control pool of strains; and, culturing the control pool in the absence of the test compound;

wherein determining whether the presence of the test compound decreases or increases the representation of a distinguishable nucleic acid sequence tag comprises comparing the representation of the tag in the pool of strains with that in the control pool.

48. The method of claim 43, wherein determining whether the presence of a test compound decreases or increases the representation of a strain in the pool of strains comprises determining the representation of each strain in the pool following culturing of the pool in the presence of the test compound.

49. The method of claim 48, wherein the representations of the strains following culturing in the presence of the test compounds are compared to the representations of the strains following culturing in the absence of the test compounds by differential hybridization with probes complementary to each nucleic acid sequence tag.

50. The method of claim 43, wherein the pool of strains comprises eukaryotic cells.

51. The method of claim 50, wherein the eukaryotic cells comprise yeast cells.

52. The method of claim 50, wherein the eukaryotic cells comprise human cells.

53. The method of claim 43, wherein determining the representation of each strain of the plurality of strains comprises hybridizing complementary probes to each distinguishable nucleic acid sequence tag in the plurality of strains.

54. The method of claim 53, wherein the complementary probes comprise at least one label, wherein, if there is more than one label, the labels may be the same as or different from each other.

55. The method of claim 54, wherein each label comprises a fluorescent moiety.

56. The method of claim 55, further comprising:
providing a first set of mixed probes comprising a fluorescent moiety producing a first color, each probe of the first set being complementary to a different nucleic acid sequence tag in the pool of strains following culturing in the presence of a test compound;
providing a second set of mixed probes comprising a fluorescent moiety producing a second color, each probe of the second set being complementary to a different nucleic acid sequence tag in the pool of strains following culturing in the absence of the test compound;
combining the first and second probes;
hybridizing the combined probes with nucleic acid sequence tag from the pool of strains cultured in the presence of the test compound to form a first hybridized array;
hybridizing the combined probes with nucleic acid sequence tag from the pool of strains cultured in the absence of the test compound to form a second hybridized array; and
observing the color of the first and second hybridized arrays whereby the color is indicative of the effect of the test compound on the representation of a strain in the pool of strains.

57. A method for evaluating the effect of a test compound in vivo on strains in a pool of microbial strains, comprising:
providing a pool of microbial strains, each strain comprising a different distinguishable nucleic acid sequence tag;
administering the pool of strains to a mammal;
administering a test compound to the mammal;
obtaining one or more samples from the mammal over a period of time;
determining whether the presence of the test compound decreases or increases the representation of one or more of the distinguishable nucleic acid sequence tags in each sample,
wherein a decrease in the representation of a tag indicates a decrease in the representation of a tagged strain and a decrease in the representation of a tagged strain indicates that the test compound decreases the proliferation of that strain and an increase in the representation of a tag indicates an increase in the representation of a tagged strain and an increase in the representation of a tagged strain indicates that the test compound increases the proliferation of that strain.

58. The method of claim 57, wherein the pool of strains comprises a plurality of strains of one species.

59. The method of claim 57, wherein the pool of strains comprises strains from a plurality of species.

60. The method of claim 57, wherein each different distinguishable nucleic acid sequence tag differs in length.

* * * * *